United States Patent [19]

Klein et al.

[11] Patent Number: 5,085,862
[45] Date of Patent: Feb. 4, 1992

[54] GENETIC DETOXIFICATION OF PERTUSSIS TOXIN

[75] Inventors: Michel H. Klein, Willowdale; Heather A. Boux, Aurora; Stephen A. Cockle, Richmond Hill; Sheena M. Loosmore, Aurora; Gavin R. Zealey, Concord, all of Canada

[73] Assignee: Connaught Laboratories Limited, Willowdale, Ontario, Canada

[21] Appl. No.: 275,376

[22] Filed: Nov. 23, 1988

[30] Foreign Application Priority Data

Nov. 24, 1987 [GB] United Kingdom ............... 8727489

[51] Int. Cl.$^5$ .............................................. A61K 39/02
[52] U.S. Cl. ................................... 424/92; 435/252.3; 530/350; 530/387; 530/403; 530/405; 530/406
[58] Field of Search ....................... 424/92; 435/252.3; 530/350, 387, 403, 405, 406

[56] References Cited

FOREIGN PATENT DOCUMENTS 0275689 7/1988 European Pat. Off. .
0322533 3/1989 European Pat. Off. .
0306318 3/1990 European Pat. Off. .

OTHER PUBLICATIONS

CA 107(21):191919S, 1987.
CA 107(1):2334p, 1987.
CA 109(25) 228114v, 1988.
CA 109(19) 165033v, 1988.
Stibitz et al., "The Construction of a Cloning Vector Designed for Gene Replacement in Bordetella Pertussus", Gene, vol. 50, 1986, pp. 133–140.
Burnette et al., "Pertussis Toxin S1 Mutant With Reduced Enzyme Activity and a Conserved Protective Epitope", Science, vol. 242, No. 4875, 1988, pp. 72–74.
Nicosia et al., Infection and Immunity, vol. 55, No. 4, 1987, pp. 963–967.
Moss et al., J. Biol. Chem., 258, 11872 [1983].
Locht and Keith, Science 232, 1258 [1986].
Carrol & Collier, Proc. Nat. Acad. Sci., U.S.A., 81, 3307 [1984].
Carroll & Collier, J. Biol. Chem., 262, 8707, [1987].
Nogimori et al., Biochem., 25, 1355 [1986].
Armstrong & Peppler, Infec. Immun., 55, 1294 [1987].
Tweten et al., J. Biol. Chem., 260, 10392 [1984].
Douglas & Collier, J. Bacteriol., 169, 4967 [1987].
Locht et al., Infect. Immun., 55, 2546 [1987].
Black et al., Ann. Sclavo, 175, [1986].
Black & Falkow, Infect. Immun., 55, 2465, [1987].
Burns et al., Infect. Immun., 55, 24, [1987].
Watkins et al., J. Biol. Chem., 260, 13478, [1985].
Arico & Rappuoli, J. Bacteriol., 169, 2849, [1987].
Nicosia et al., Proc. Nat. Acad. Sci., U.S.A., 83, 4631 [1986].
Ditta et al., Plasmid, 13, 149, [1985].

*Primary Examiner*—Paul J. Killos
*Attorney, Agent, or Firm*—Sim & McBurney

[57] ABSTRACT

A new method is described for the preparation of a safe, immunogenic and efficacious vaccine for protection against the disease pertussis. In development of this vaccine, specific functional sites of pertussis toxin have been identified, and using this information, defined mutant holotoxins have been produced by site directed mutagenesis of the toxin gene. A number of these toxin analogues are detoxified, retain an immunodominant S1 epitope, are immunoganic and are protective in the standard pertussis vaccine potency test in mice.

16 Claims, 21 Drawing Sheets

FIG. 1.

AMINO ACID SEQUENCE OF RADIO LABELLED PEPTIDES

| CYCLE NO. | | | | | 5 | | | | | 10 | | | 15 | |
|---|---|---|---|---|---|---|---|---|---|---|---|---|---|---|
| PEPTIDE A | Ile | Leu | Ala | Gly | Ala | Leu | Ala | Thr | Tyr | Glu | Ser | * | Tyr | Leu | Ala |
| PEPTIDE B | Ile | Leu | - | Gly | Ala | Leu | Ala | Thr | Tyr | Glu | Ser | * | Tyr | Leu | Ala |
| | | | | | | | | | | | | | | | |
| SUBUNIT S1 | Ile | Leu | Ala | Gly | Ala | Leu | Ala | Thr | Tyr | Glu | Ser | Glu | Tyr | Leu | Ala |
| RESIDUE NO. | | | | | 120 | | | | | 125 | | | 130 | |

\* UNCHARACTERIZED RADIOACTIVE AMINO ACID FOUND AT CYCLE 12

− NO AMINO ACID WAS IDENTIFIED AT THIS CYCLE

λgt II 15-4-1

λCh 35  Ch III

FIG.5(iii).

```
CCG CTC AAC GGA TAT TGC GAATGAACCCTTCCGGAGGTTTCGACGTTCCGCGCAATCGCTTGAGACGATCTTCCGCCCTGGTTCATTCCGGAACACCGCAAC
PRO LEU ASN GLY TYR CYS GLU
                                                                                              S3
ATG CTG ATC AAC AAC AAG AAG CTT CAT CAC ATT CTG CCC ATC CTG GTG CTC GCC CTG CTG GGC ATG CGC ACG GCC CAG GCC
*MET LEU ILE ASN ASN LYS LYS LEU HIS HIS ILE LEU PRO ILE LEU VAL LEU ALA LEU LEU GLY MET ARG THR ALA GLN ALA
 S3
GTT GCG CCA GGC ATC GTC ATC CCG AAG CCG CCG AAG CAG CAG GGC GGC GCC TAT GGA CGC TGC CCG AAC GGA ACC CGC
VAL ALA PRO GLY ILE VAL ILE PRO LYS PRO PRO LYS GLN GLN GLY GLY ALA TYR GLY ARG CYS PRO ASN GLY THR ARG
  1       3       5       7       9      11      13      15      17      19      21      23      25      27  28
                  2       4       6       8      10      12      14      16      18      20      22      24      26
GCC TTG ACC GTG GCC GAA GGC AAC GCC GAA TTG CAG GAG ACG TAT TTG CGC CAG ATA ACG CCC GGC TGG TCC ATA TAC GGT
ALA LEU THR VAL ALA GLU GLY ASN ALA GLU LEU GLN GLU THR TYR LEU ARG GLN ILE THR PRO GLY TRP SER ILE TYR GLY
 29      31      33      35      37      39      41      43      45      47      49      51      53      55  56
     30      32      34      36      38      40      42      44      46      48      50      52      54
CTC TAT GAC GGT ACG CTG GGC CAG GCG TAC GGG ATC ATC AAG GAC GCG CCA GGC GCG GGG TTC ATT TAT CGC GAA
LEU TYR ASP GLY THR LEU GLY GLN ALA TYR GLY ILE ILE LYS ASP ALA PRO GLY ALA GLY PHE ILE TYR ARG GLU
 57      59      61      63      65      67      69      71      73      75      77      79      81  82 83 84
     58      60      62      64      66      68      70      72      74      76      78      80
ACT TTC TGC ATC ACG ATA TAC AAG ACC GGG CAA CCG GCT GCG GAT CAC GAC ACG AAG GTC ACG GCC ACG CGC CTG CTC
THR PHE CYS ILE THR ILE TYR LYS THR GLY GLN PRO ALA ALA ASP HIS ASP THR LYS VAL THR ALA THR ARG LEU LEU
 85      87      89      91      93      95      97      99     101     103     105     107     109     111 112
     86      88      90      92      94      96      98     100     102     104     106     108     110
GCC AGC ACC AAC AGC AGG CTG TCC GCG GTA TTC GTC AGG GAC GGG CAA TCG GTC ATC GGA GCC TGC AGC CCG TAT GAA GGC
ALA SER THR ASN SER ARG LEU CYS ALA VAL PHE VAL ARG ASP GLY GLN SER VAL ILE GLY ALA CYS SER ALA SER PRO TYR GLU GLY
113     115     117     119     121     123     125     127     129     131     133     135     137     139 140
    114     116     118     120     122     124     126     128     130     132     134     136     138
AGG TAC AGA GAC ATG GAC GCG ATG TAC TAC CTG CTG TAC ATG TCC GGC CTT GCC GTA CGC GTC CAC GTC AGC
ARG TYR ARG ASP MET ASP ALA MET TYR TYR LEU LEU TYR MET ILE SER GLY LEU ALA VAL ARG VAL HIS SER
141     143     145     147     149     151     153     155     157     159     161     163     165 166 167 168
    142     144     146     148     150     152     154     156     158     160     162     164
AAG GAA GAG CAG TAT TAC GAG GAC TAC TTC CAG ACA TTC GCC GCC ATT TCC CTC ACC TGC AAC CCG GCA GCG
LYS GLU GLU GLN TYR TYR GLU ASP TYR PHE GLN THR PHE ALA ALA ILE SER LEU THR CYS ASN PRO ALA ALA
169     171     173     175     177     179     181     183     185     187     189     191     193 194 195 196
    170     172     174     176     178     180     182     184     186     188     190     192
TCG ATA TGC TGAGCCGCCGGCTGCACCTGTGTTCCCCAGCGTCGTCCATGTTTTTCCTTGACGATACGCGAATGAATCCCTTGAAGACTTGAGACATCCGTACCGCGCCT
SER ILE CYS
197 198 199
GGCCCTTCATGGCAGCCTGCAGTCGGCCACGCGTTCAGTCGCCACGTGGCAGTCGGCCATCGTCCCGCAGCCTCCCGCAGCGGCCATCGTGGTCGTACTG
CGGCCGCGTCAGTGCCCAGTGGCCATCGCCCGAAATCGCTGACCTGAGACCTGACAGCTCGTTCCCGCAGCTGCTGACGTGCTGCCAGTGGTCTGCGGGACTGC
TGATCGGCCATCGGCCCAACATCCGCTGCTGATATCGGAACATCGGAACATGCTGCGCTTTCAAGGCGTATCGGCCATCGTCGCCGCACCGCGGCCATCGATCGG
CGTACCCGCGATGGCCTGGCAGCCGGCGATCGCACGCGAGCCATCGGTTGCCCGCTGCTGATGGCATCCAGCATCGCCTTTCTGCCCGTTGTTCCGGTGTTCCGGCT
ATGATCCGCGGCCGATGACCAGCAGTTCCGCCTGATC
```

✦DENOTES THE LOCATION OF MUTATIONS IN THE S₁ GENE

GENETIC DETOXIFICATION OF PERTUSSIS TOXIN

FIELD OF INVENTION

The present invention relates to a novel method for the detoxification of pertussis toxin by the genetic manipulation of DNA segments coding for one or more amino acid residues essential for the toxin's biological activity. It also relates to a procedure for the creation of genetically altered *Bordetella pertussis* bacteria that produce the said detoxified pertussis toxin.

BACKGROUND OF THE INVENTION

Whooping cough, or pertussis, is a severe, highly contagious respiratory disease of infants and young children caused by infection with *Bordetella pertussis*. Owing to the many virulence factors associated with this organism, the pathogenesis of the disease is still not fully understood; however, it is generally recognized that the major systemic effects are caused by pertussis toxin (PT). This material exhibits a wide range of biological activities as illustrated by such alternative names as lymphocytosis-promoting factor, histamine-sensitizing factor and inlet-activating protein. Many of these effects are associated with its biochemical function as an adenosine diphosphate (ADP)-ribosyltransferase. ADP-ribosylation of certain acceptor guanosine triphosphate-binding proteins leads to a loss of control over a variety of metabolic pathways mediated by cyclic adenosine monophosphate and by phospholipase C. In the absence of a protein acceptor, PT also catalyses the hydrolysis of nicotinamide adenine dinucleotide (NAD glycohydrolase activity).

Conventional killed whole-cell pertussis vaccines contain a mixture of antigens and there has been a great deal of work towards the development of a defined acellular vaccine comprising specific protective antigens. PT is the most significant protective antigen. Other antigens under consideration are agglutinogens and filamentous hemagglutinin (FHA).

Normally PT and other antigens are chemically inactivated, or toxoided, using agents such as formaldehyde, glutaraldehyde or hydrogen peroxide. This approach has the serious disadvantage that a delicate balance must be sought between too much and too little chemical modification. If the treatment is insufficient, the vaccine may retain residual toxicity owing to the presence of a small proportion of unchanged virulence factors including PT. If the treatment is too excessive, the vaccine may lose potency because its native immunogenic determinants are masked or destroyed. This problem is of particular concern in the case of PT, since the catalytic subunit is comparatively difficult to inactivate by aldehydes. The possible residual toxicity or reversion of toxoided whole-cell pertussis vaccines has been questioned for many years, and it has suggested that in rare cases the vaccine might cause major neurological damage. All pertussis vaccines that are in use at present, or in the trial stages, depend on the inactivation of the antigens by chemical means, which introduces the problems previously mentioned. It is obvious that if an inactivated vaccine could be designed without resorting to the toxoiding process, but preserving the native structure of immunogenic and protective epitopes, an additional degree of safety and efficacy would be added. For these reasons the inventors have genetically manipulated the gene coding for $P_TTOX$, and constructed strains of *B. pertussis* that secrete non-toxic PT analogues.

In its structural organization, PT belongs to the family of ADP-ribosyltransferase bacterial toxins, which also includes diphtheria toxin, *Pseudomonas aeruginosa* exotoxin A, cholera toxin and *Escherichia coli* heat labile toxin. Accordingly, it consists of two functional moieties: an A portion, which carries the enzymic activity, and a B portion, which binds to the host cell and permits translocation of the A portion to its site of action. In PT, the A portion is a discrete subunit, commonly denoted S1. The B portion is a non-covalent oligomer of five polypeptides arranged as two dimers, comprising subunits S2 plus S4 and subunits S3 plus S4 respectively, held together by a joining subunit S5.

The amino acid sequence of the S1 subunit reveals several features of interest. There are only two cysteine residues which form an intrachain disulphide bond; however, it is known that for enzymic activity the toxin must be reduced (Moss et al., J. Biol. Chem. 258, 11872, [1983]), indicating the importance of these residues. There are two tryptophans in S1, and it has been suggested that tryptophan residues are close to the NAD binding sites of diphtheria toxin and *P. aeruginosa* exotoxin A. Two conserved regions in S1 are also found in the amino acid sequences of cholera toxin and *E. coli* heat labile toxin (Locht & Keith, Science, 232, 1258, [1986]). In addition the NAD active sites of diphtheria toxin and *P. aeruginosa* exotoxin A have been shown to contain a glutamic acid residue (Carrol & Collier, Proc. Nat. Acad. Sci., U.S.A., 81, 3307, [1984]; Carrol & Collier, J. Biol. Chem., 262, 8707, [1987]).

As noted above, the B portion of PT mediates its binding to cellular receptors and contains two dimers. Whether each of these dimers bears a binding site remains controversial. However, the S2 and S3 subunits are similar in amino acid sequence and binding studies have indicated that lysine and/or tyrosine residues of S3 in particular are implicated in the interaction of the toxin with its receptor. (Nogimori et al., Biochem., 25, 1355, [1986]; Armstrong & Peppler, Infect. Immun., 55, 1294, [1987]).

Site-directed mutagenesis of diphtheria toxin and *P. aeruginosa* exotoxin A at the NAD-interacting glutamic acid residues has led to significant reduction in ADP-ribosyltransferase activity (Tweten et al., J. Biol. Chem., 260, 10392, [1984]; Douglas & Collier, J. Bacteriol., 169, 4967, [1987]). Complete truncated forms of S1 and S2 have been expressed in *E. coli* (Locht et al., Infect. Immun., 55, 2546, [1987]). Mutations of the TOX operon generated by transposon insertion, gene truncation or linker insertion have been introduced by allelic exchange into the chromosome of *B. pertussis* (Black et al., Ann. Sclavo, 175, [1986]; Black & Falkow, Infect. Immun., 55, 2465, [1987]). However, the biological and immunoprotective properties of fully-assembled recombinant holotoxins specifically detoxified by site-directed mutagenesis of functional amino acid residues have not been reported. The generation of such PT analogues for inclusion in a safe and efficacious pertussis vaccine is the subject of this invention.

In testing for the efficacy and toxicity of materials that could be candidates for a protective vaccine, there are a number of in vivo and in vitro assays available. The standard test for potency is the mouse protection test, which involves intra-cerebral challenge with live *B. pertussis*. Newer vaccine tests measure the production of protective antibodies. A common toxicity test is the CHO (Chinese hamster ovary) cell clustering assay, which reflects both the ADP-ribosyltransferase and binding ability of the toxin (Burn et al., Infect. Immun., 55, 24, [1987]). A direct test of the enzymic activity of PT is the ADP-ribosylation of bovine transducin (Walkins et al., J. Biol. Chem., 260, 13478, [1985]).

SUMMARY OF INVENTION

In accordance with the present invention, there is provided a novel method of detoxifying PT, which does not suffer from the drawbacks of the prior art chemical methods and yet provides an detoxified PT that retains its immunological properties without possessing undesirable side effects. In the present invention, amino acid residues of the toxin that are crucially important to its functional and toxic activities are identified. These residues are subsequently removed or replaced by site-directed mutagenesis of the isolated toxin gene. The mutated toxin operon resulting from such manipulations then is substituted for the native gene in the organism, which thereby produces the non-toxic analog of the toxin under normal growth conditions. In this manner, the three-dimensional structure and thus the immunogenicity of the PT analogue is minimally impaired. Indeed, an appropriate mutant form of the toxin on its own may provide satisfactory protection against the severe symptoms of pertussis, though other components may be required to establish resistance against the bacterial infection itself.

In accordance with one aspect of the present invention, therefore, there is provided an immunoprotective genetically-detoxified mutant of pertussis toxin. By the term "genetically-detoxified" as used herein is meant a pertussis toxin mutant which exhibits a residual toxicity of about 1% or less, preferably less than about 0.5%, of that of the native toxin. The residual toxicity is determined by CHO cell clustering assay and ADP-ribosyltransferase activity.

In accordance with another aspect of the present invention, there is provided a vaccine against *Bordetella pertussis* comprising an immunogenically-effective amount of the immunoprotective mutant of pertussis toxin or a toxoid thereof and a physiologically-acceptable carrier therefor. The genetically-detoxified pertussis toxin also may be used as a carrier protein for hapten, polysaccharides or peptides to make a conjugate vaccine against antigenic determinants unrelated to the toxin.

A further aspect of the present invention provides a method of production of the mutant, which comprises identifying at least one amino acid residue of the toxin which confers toxicity to the toxin; effecting site-directed mutagenesis of the toxin gene to remove or replace at least one such residue and to produce a mutated toxin operon; substituting the mutated toxin operon for the native gene in the *Bordetella pertussis* organism; and growing the transformed organism to produce an immunoprotective, genetically-detoxified toxin.

As will be apparent from the following disclosure, the present invention further provides novel strains of *Bordetella pertussis* from which the toxin operon has been removed or has been replaced by a mutant gene as provided herein.

BRIEF DESCRIPTION OF DRAWINGS

FIG. 1 shows the sequences of amino acids obtained by automated sequencing of radiolabelled peptides A from subunit S1 which B and are compared with residues from mature S1;

FIGS. 5(I-III) shows the nucleotide sequence and structural gene translation products of the *B. pertussis* 10536 TOX gene;

GENERAL DESCRIPTION OF INVENTION

Figure 5I:
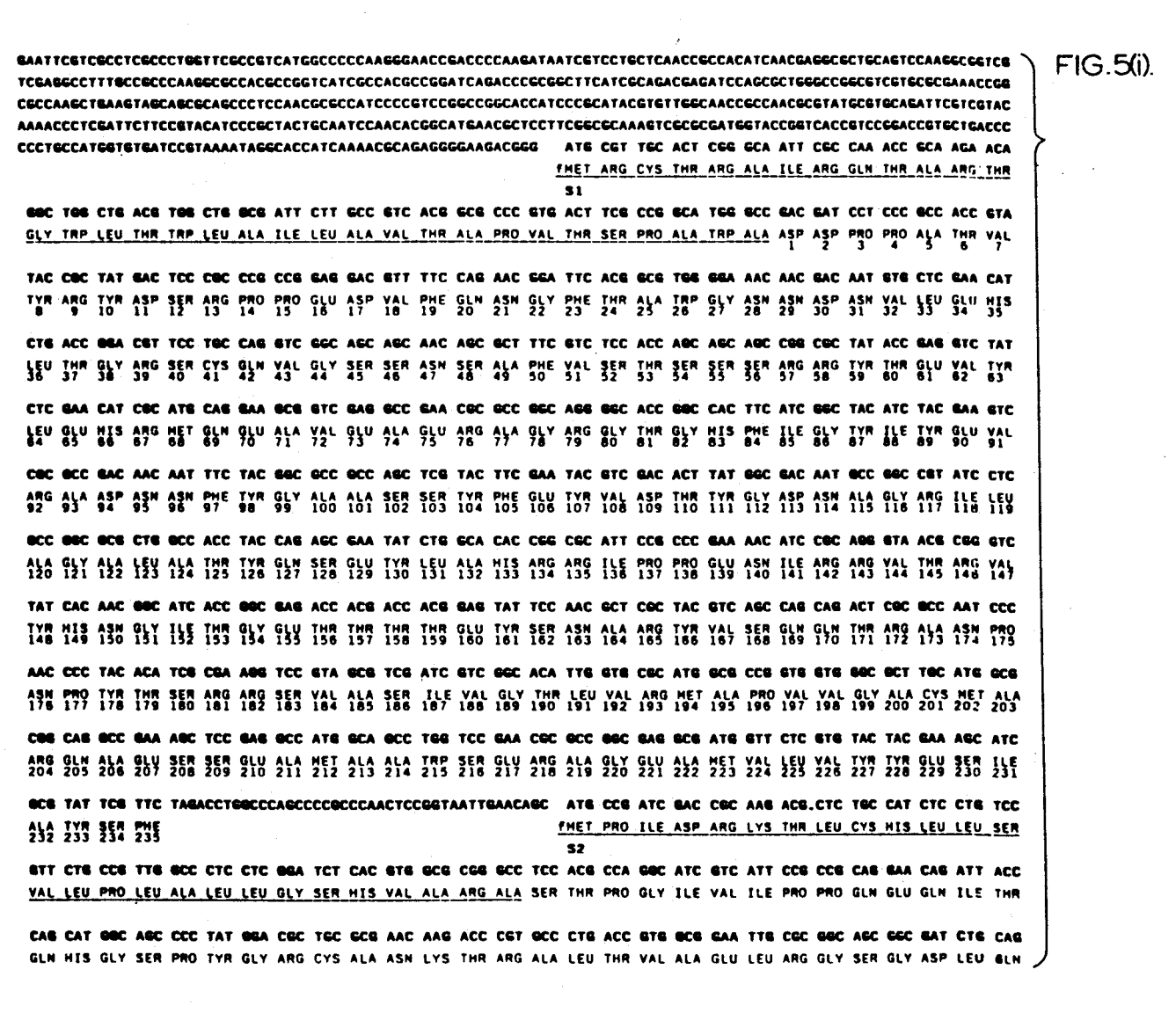
Figure 5II:
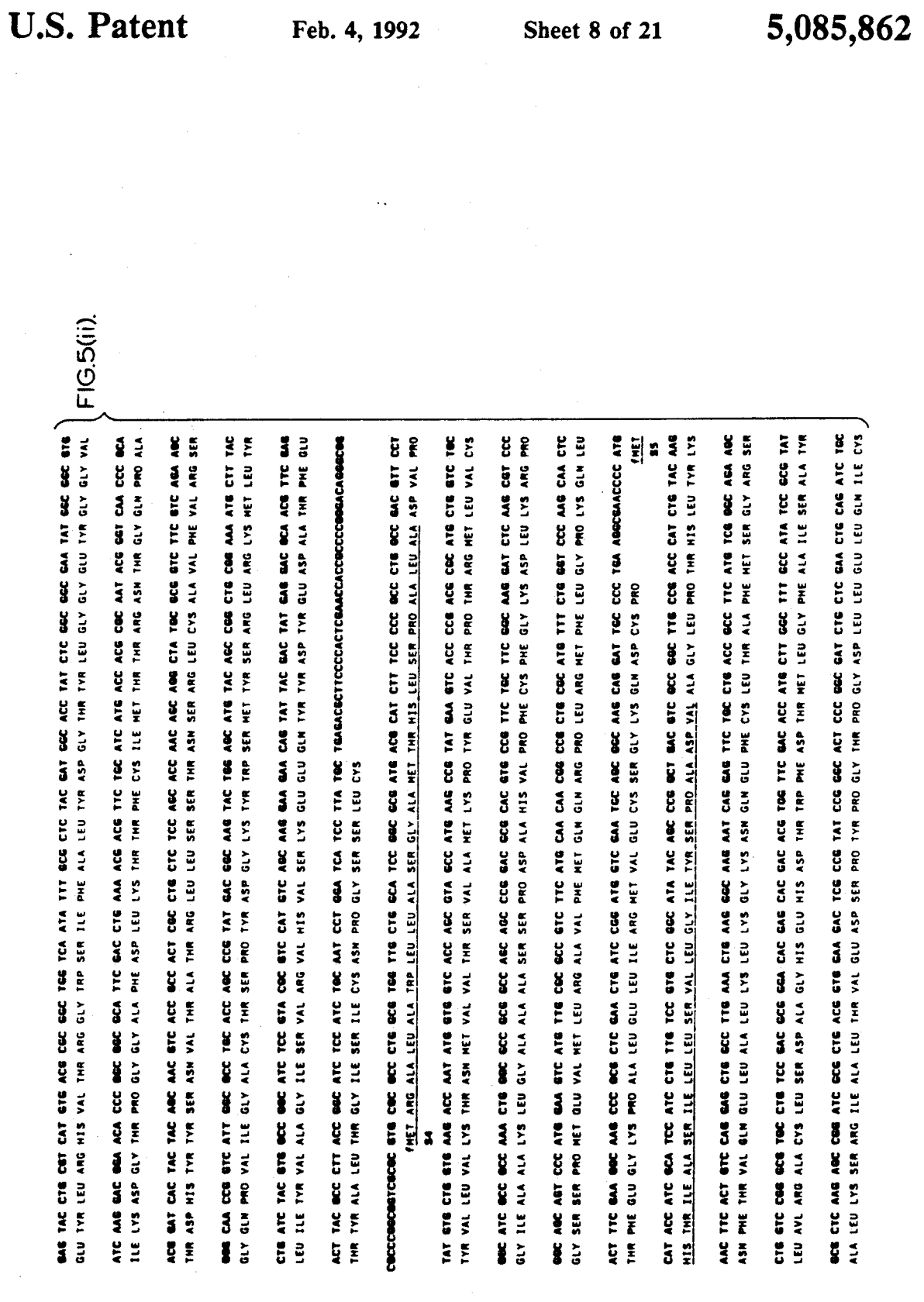
Figure 2:
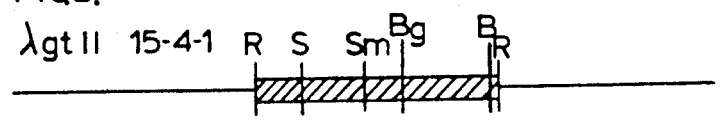
FIGS. 2A-E shows the structures of various TOX clones obtained from the chromosomal libraries.
Figure 2B:
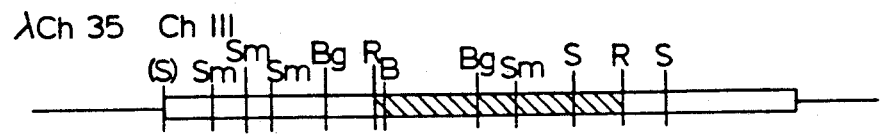
Figure 2C:
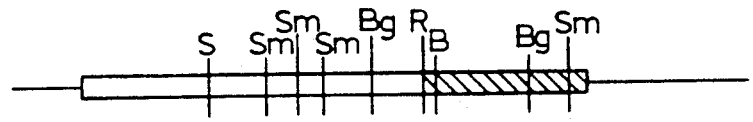
Figure 2D:
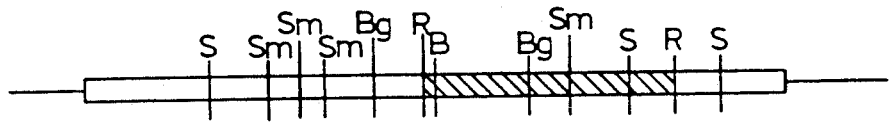
Figure 2E:
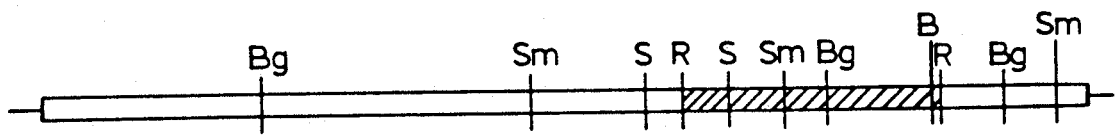

It has been shown that the TOX operons from different strains of *B. pertussis* are nearly identical in sequence (Nicosia et al, Proc. Nat. Acad. Sci., U.S.A., 83, 4631, [1986]; Locht & Keith, Science, 232 1258, [1986]). The TOX locus is here defined as a DNA fragment beginning at the EcoR I cleavage site which encodes a 5'-flanking sequence, the promoter region, the structural genes for all PT subunits and a 3' flanking sequence. The TOX gene from *B. pertussis* 10536, which is the strain used by the inventors, was cloned and sequenced. Its nucleic acid sequence was found to be highly homologous to other published sequences, with four unique base differences downstream from the G of the EcoR I site defined as base 1. The complete nucleotide and corresponding amino acid sequences of the structural genes are shown in FIG. 5.

The plasmid DNA of clone J-169-1 which contains the TOX gene from *Bordetella pertussis* 10536 cloned into pUC8:2 as a 4.6 kb EcoR I, BamHI fragment, has been deposited with the American Type Culture Collection (ATCC) in Rochville, Md., U.S.A. on Nov. 24, 1988 under American No. 40518.

The T at position 315 is unique to strain 10536 and there are three differences in the S1 gene at positions 710, 1200 and 1202, resulting in two unique amino acids, glutamic acid and valine, at positions 34 and 198 of the mature S1 sequence, respectively. The toxin genes of *B. parapertussis* and *B. bronchiseptica* are not expressed because of multiple mutations in their promoter regions, (Arico & Rappuoli, J. Bacteriol., 169, 2849, [1987]). This has allowed the use of *B. parapertussis* as a host for the expression of mutated toxin genes for screening purposes.

The inventors have shown that substitution of a single amino acid in S1, in particular at the active site for NAD hydrolysis (position 129), virtually abolishes the ADP-ribosyltransferase activity of PT. However, it may be desirable to alter several sites on the holotoxin to ensure complete safety. Accordingly, this invention applies to single or multiple mutations in both or either of the A and B portions of the toxin to abolish toxicity, and to the reinsertion of these mutations back into the genome of Tox⁻ strains of Bordetella.

A number of strategies have been used by the inventors to determine regions of the toxin that might be closely associated with its biological activities, and might, therefore, contain candidate sites for genetic manipulation.

PT was prepared from culture supernatants of *B. pertussis* (strain 10536). The crude solution was concentrated by ultrafiltration and passed through a fetuin-agarose affinity column to adsorb PT. PT was eluted from the washed column using potassium thiocyanate and dialyzed into a phosphate-saline medium. At this stage, the purity was 90-95%, as determined by sodium dodecyl sulphate-polyacrylamide gel electrophoresis (SDS-PAGE) analysis. The major contaminant was FHA. Further purification was achieved by chromatography through a hydroxyapatite column, giving a material with a purity >99%.

The site of interaction of the S1 subunit with NAD was determined by photo-crosslinking NAD to isolated and purified S1 using [$^{14}$C]NAD, labelled either in the nicotinamide carbonyl group or the adenine moiety. Radiolabel was efficiently transformed from the nicotinamide moiety into the protein. The protein was then digested with trypsin and chromatographed on an HPLC column, giving two major radioactive peptides. After purification the two tryptic peptides were sequenced which demonstrate that the first fifteen residues corresponded to residues. 118-132 of mature S1. In both the peptides, radioactivity was associated with an unidentified amino acid corresponding to position 129 in mature S1. Radioactivity was not detected in any other position. This established that GLU$^{129}$ is the site of photo-crosslinking of NAD and is therefore likely to be an important component of the nicotinamide interaction site. Significantly the sites of linkage in diphtheria toxin and *P. aeruginosa* exotoxin A are also glutamic acid residues and the three amino acid sequence commencing at GLU$^{129}$ of S1 resembles the analogous sequences of the other bacterial toxins.

Chromosomal DNA was prepared from *B. pertussis* (strain 10536) and was digested with the restriction enzyme EcoR I in such a way that fragments were obtained ranging in size from a few hundred bases to a few kilobases. The DNA fragments were ligated with λ gt11 DNA which had been digested with EcoR I and dephosphorylated. The DNA was packaged into phage particles and maintained in *E. coli* Y1090 as a gt11 *B. pertussis* genomic library. Alternatively, *B. pertussis* chromosomal DNA was digested with the restriction enzyme Sau3A I to generate very large DNA fragments which were ligated with BamH I restricted λ Charon 35 DNA. The DNA was packaged into phage particles and maintained in *E. coli* LE392 as a λ Ch 35 *B. pertussis* genomic library.

These genomic libraries were plated and phage plaques transferred onto nitrocellulose filters. The filters were screened by DNA hybridization using an oligonucleotide probe specific for the PT S4 subunit. Positive plaques were further purified by two additional rounds of plating and hybridization. Phage DNA was prepared from the positive plaques and subjected to restriction enzyme digestion and Southern blot analysis. Clones containing the entire 4.6 kb EcoR I pertussis toxin operon (TOX) or portions thereof and with differing 5'- or 3'-flanking regions were characterized. The TOX gene was subcloned for sequence analysis and further genetic manipulation. Sequencing was performed using the dideoxy chain termination method and the results indicated four novel bases in the 10536 TOX gene as compared to published sequences.

Subclones of S1 or S3 genes in M13 phage were subjected to in vitro site-directed mutagenesis using the phosphorothioate procedure. Single-stranded DNA from these clones was annealed with oligonucleotide primers specifically designed to mutate or delete one or more amino acids. The mutagenesis was carried out using a kit available from a commercial source. Mutations were verified by sequencing of single-stranded phage DNA. Mutant subunit genes were recombined with the remainder of the operon to construct mutant holotoxin genes in the broad-host-range plasmid pRK404 maintained in *E. coli* JM109.

Figure 7:
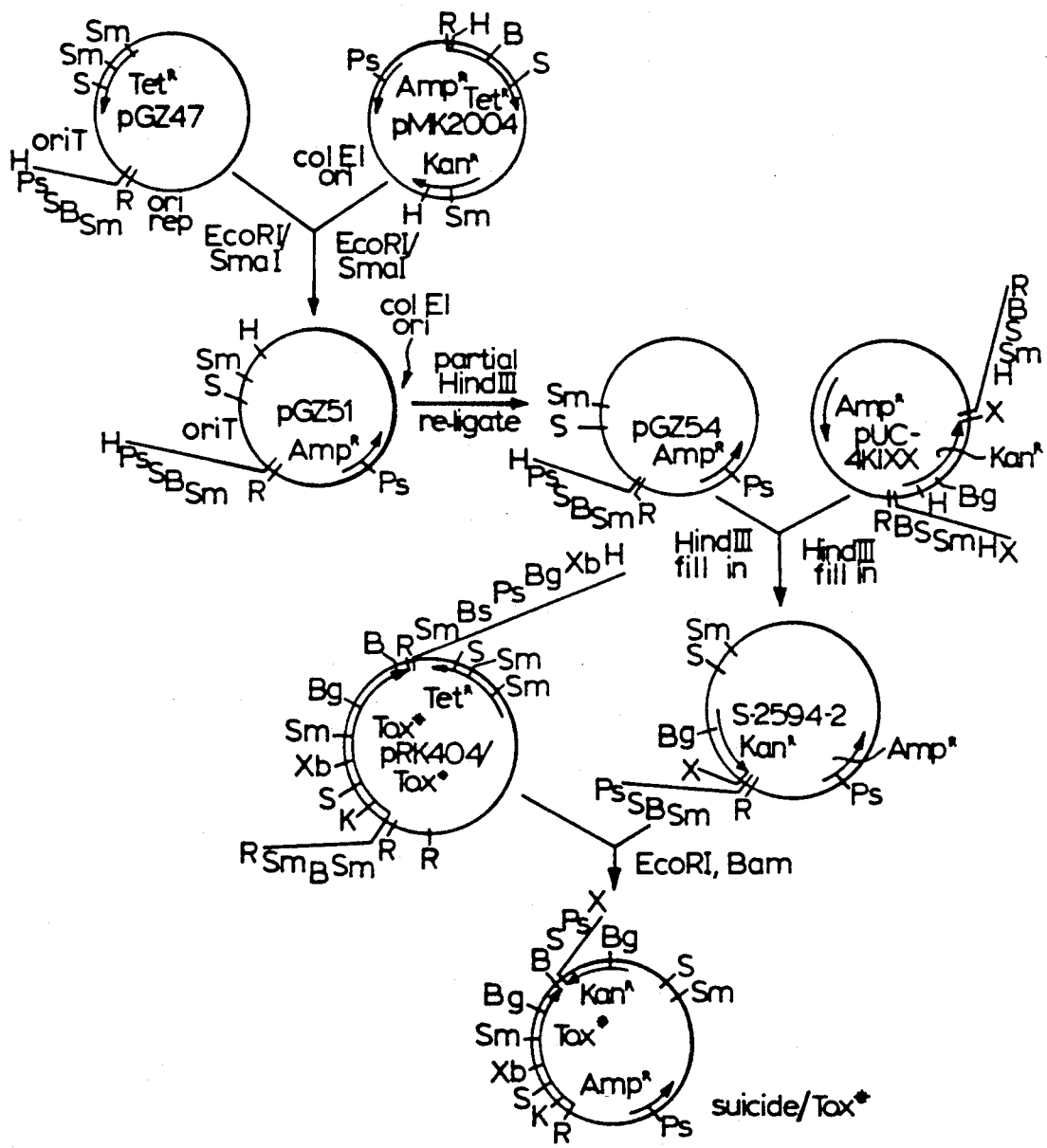
FIG. 7 shows the development of a "suicide" plasmid, one capable of conjugative transfer but not replication, based on pRK404 and pMK2084 (Kahn et al., Methods in Enzymology, 68, 278, [1979]), for non-homologous recombination. The final plasmids also contain a kanamycin resistance gene 3' of the TOX or TOX analogue genes.

In order to characterize the holotoxin analogues, these plasmids were transferred to a spontaneous streptomycin-resistant *B. parapertussis* strain by conjugation on a solid surface, using pRK2013 as a helper plasmid. The colonies were selected on streptomycin and tetracycline-containing Bordet-Gengou blood plates. Mutated genes were also integrated into the chromosome of *B. parapertussis* by conjugative transfer of a suicide plasmid. The integration was either random or directed through homologous recombination utilizing the flanking regions of the *B. pertussis* TOX operon. FIG. 7 shows the construction of a suicide plasmid containing mutants for random recombination.

Liquid cultures were grown in modified Strainer-Scholte medium containing methyl-β-cyclodextrin in shake flasks (10 ml to 2 L) or in fermentors (20 L to 50 L). The expression level of holotoxin analogues in culture supernatants was determined by enzyme-linked immunosorbent assay (ELISA) and found to vary with the mutation. The residual toxicity of the analogues was measured by the CHO cell clustering assay.

A number of PT analogues were purified from 2 L to 50 L cultures of recombinant B. pertussis strains, according to methods described in detail for native PT. The ADP-ribosyltransferase activity of these mutants was determined as the extent of incorporation of radioactivity into bovine transducin from [$^{32}$P]-labelled NAD. Table 1a below lists the PT mutants generated and Table 1b below summarizes their residual toxicity and enzymic activity.

Selected purified mutants were tested in mice for acute toxicity, histamine sensitization activity and potency in the standard mouse intracerebral challenge test. These results are presented in Table 2 below and show that PT analogues have a markedly-decreased acute toxicity and histamine sensitization activity and that they are immunoprotective in the mouse potency test.

the immunological properties of PT analogues were further investigated by epitope mapping and by analysis of the antibody response in mice. Several monoclonal antibodies (MAbs) specific for individual subunits or dimers of PT were prepared and used to determine by ELISA whether the epitopes defined by these antibodies were affected by the mutations. The S1 epitope recognized by MAb PS21 is of particular significance, since it is immunodominant in mice and this antibody confers passive protection in the mouse intracerebral challenge test. (The hybridoma which secretes the monoclonal antibody PS21 has been deposited with ATCC on Nov. 30, 1989 under accession No. HB 10299.) The preservation of this epitope in the PT analogues is indicated in Table 1b.

Immunogenicity studies in mice were performed on three purified PT mutants. Immune sera were tested for their ability to inhibit PT-induced CHO cell clustering (Table 3 below), and for their anti-PT, anti-S1 and anti-B-oligomer antibody titres by indirect ELISA (Table 4 below).

To generate a B. pertussis strain expressing a mutated TOX gene suitable for vaccine production, the endogenous TOX operon was deleted by homologous recombination using electroporation of linear B. pertussis DNA containing the 5'- and 3'-flanking regions of the TOX locus. Selected mutant genes were then reintegrated into the TOX locus of the B. pertussis chromosome. Clones containing mutated TOX genes were grown and the culture supernatants assayed for level of expression of PT analogues and their residual toxicity as previously described. These results are shown in Table 5 below.

Certain Bordetella pertussis strains wherein the TOX gene has been removed entirely or has been replaced by certain clones, have been deposited with ATCC on Nov. 23, 1988, as follows:

| Strain | Modification | ATCC Accession Number |
| --- | --- | --- |
| B. pertussis 29-9 | TOX deleted | 53838 |
| B. pertussis S-2962-2-1 | S1:GLN$^{129}$ | 53836 |
| B. pertussis S-2962-1-2 | S1:GLY$^{129}$ | 53837 |
| B. pertussis S-3036-2 | S1:GLU$^{58}$ | 53835 |
| B. pertussis S-3122-3-1 | SA:ALA$^{41}$ | 53834 |
| B. pertussis S-3122-2-3 | S1:GLY$^{129}$ S3:ASN$^{92}$ARG$^{93}$ | 53833 |

The Tox$^-$ strain is a novel strain of Bordetella pertussis from which the toxin operon has been removed and from which foreign DNA is absent and which is capable of being grown in the absence of antibiotics to produce B. pertussis antigens free of pertussis toxin.

Each of the transformed strains is a strain of Bordetella pertussis in which the toxin operon has been replaced by a mutant gene formed by site-directed mutagenesis of at least one specific amino acid residue responsible for pertussis toxin toxicity.

The data presented herein demonstrate that the inventors have produced a series of pertussis toxin analogues that exhibit a substantial reduction in CHO cell clustering and enzymic activities (0.1 to 1% of the wild-type activity). Many of these analogues also maintain an immunodominant S1 epitope recognized by a protective monoclonal antibody. Moreover, certain of these mutants have been shown to protect mice against challenge with virulent B. pertussis at doses that exhibit minimal toxicity. While the majority of these results have been generated using PT mutants secreted by B. parapertussis, it is evident that equivalent products are obtained by genetic manipulation of B. pertussis itself. This disclosure, therefore, presents a number of detoxified immunogenic forms of pertussis toxin that would be candidates for inclusion in a novel pertussis vaccine, and a method for producing them in B. pertussis.

EXAMPLES

Methods of molecular genetics, protein biochemistry and fermentation and hydridoma technology used but not explicitly described in this disclosure and these Examples are amply reported in the scientific literature and are well within the ability of those skilled in the art.

EXAMPLE I

This Example illustrates the preparation and purification of PT.

Culture supernatants of B. pertussis (strain 10536) were concentrated 20–50 times by ultrafiltration through a 10,000 or 20,000 molecular weight cut-off membrane using a Millipore Pellicon cassette system. The toxin was adsorbed from crude concentrates by passage through a fetuin-agarose affinity column equilibrated with 1M potassium phosphate, 10 mM NaCl at pH 7.5. The volume of adsorbent was typically 1 ml per mg of toxin. The loaded column was washed with 100 mM potassium phosphate, 1M NaCl at pH 7.5, then eluted with the same buffer containing 3M potassium thiocyanate to desorb the toxin. Pooled fractions were dialyzed against 50 mM Tris-HCl, 200 mM NaCl containing 10% v/v glycerol at pH 8.0, to remove thiocyanate, then against 50 mM Tris-HCl, 200 mM NaCl containing 50% v/v glycerol at pH 8.0, to allow storage of the product at $-200°$ C. The yield as determined by ELISA was typically 90-95%. The purity as determined by SDS-PAGE was 90-95%, the major contaminant being FHA. For further purification the stored toxin was diluted five-fold with water and loaded onto a hydroxyapatite column of volume 1 ml per mg of toxin, that had been equilibrated with 10 mM potassium phosphate at pH 8.0. The column was washed with 30 mM potassium phosphate at pH 8.0 then eluted with 100 or 200 mM potassium phosphate to desorb the toxin. Pooled fractions were dialyzed against 100 mM potassium phosphate containing 50% v/v of glycerol at pH 8.0 and the final product stored at 200° C. The yield was typically 90-95%, and the purity >99% as shown by SDS-PAGE.

EXAMPLE II

This Example illustrates the preparation of PT subunit S1.

PT was adsorbed to fetuin-agarose as described in Example I, then the column was washed with CHAPS buffer (500 mM urea, 50 mM potassium phosphate, 100 mM NaCl and 1% w/v of CHAPS(3-[(3-cholamidopropyl)-dimethylammonio]-1-propanesulphonate) at pH 7.5). The column was eluted with the same medium containing 500 μM of adenosine triphosphate (ATP). The S1 subunit emerged as a sharp peak at the column volume. The pooled fractions were passed through a clean fetuin-agarose column equilibrated with CHAPS-/ATP buffer to remove residual B oligomer, then dialyzed against 100 mM potassium phosphate containing 50% v/v glycerol at pH 8.0 for storage at $-200°$ C. S1 was quantified by reverse-phase HPLC on a Vydac C4 column by comparison of the integrated peak area with that of a PT standard. The yield was typically only 20-25%, but the product was free of other subunits as demonstrated by both SDS-PAGE and reverse-phase HPLC.

EXAMPLE III

This Example illustrates the photocrosslinking of NAD to the S1 subunit.

Reaction mixtures (100 μl) containing 50 μg/ml of S1, 10 mM dithiothreitol and 50 μM NAD in CHAPS buffer were placed in the wells of a 96-well microtitre plate set in ice, preincubated for 30 min and then irradiated at 254 nm for periods up to 3 hr at a distance of 5 cm with a 9 W mercury lamp. Samples were then assayed for residual NAD glycohydrolase activity. The enzyme activity of S1 was completely abolished after irradiation for 2 hr, whereas the extent of photoinactivation was only 40% under the same conditions but in the absence of NAD. This result indicated that NAD-dependent photochemical events had occurred. To discover which part of the NAD molecule interacted with the protein and the extent of crosslinking, S1 was irradiated under identical conditions with [carbonyl-$^{14}$C]NAD or [adenine-$^{14}$C]NAD. Aliquots were removed at intervals up to 3 hr and treated with trichloroacetic acid (TCA) to 10% w/v. The precipitated protein was collected by filtration, washed with fresh 10% w/v TCA and counted in a scintillation counter. Results indicated that the radiolabel was incorporated from the nicotinamide moiety rather than from the adenine moiety, and that the extent of incorporation was 0.75 mol label per mol protein.

EXAMPLE IV

This Example identifies the site of photocrosslinking on the S1 subunit.

Reaction mixtures (3 ml) containing 100 μg/ml of S1, 10 mM dithiothreitol and 50 μM [carbonyl-$^{14}$C]NAD in CHAPS buffer were placed in a Petri dish on ice to give a 1 mm layer, then irradiated at 254 nm for 2 hr with gentle magnetic stirring. The solution was deaerated with nitrogen, further reduced with dithiothreitol and S-alkylated with 4-vinylpyridine to prevent oxidation of thiol groups. The reaction mixture was dialyzed extensively against 10 mM acetic acid and the radiolabelled protein was collected after precipitation with 20% w/v TCA.

The precipitated protein (1 mg) was redissolved in 2M urea, 200 mM ammonium bicarbonate to 500 μg/ml and digested with 50 μg/ml trypsin for 20 hr at 37° C. The mixture was acidified and fractionated on a 1×25 cm Vydac $C_{18}$ reverse-phase HPLC column, using a linear gradient of 0–50% acetonitrile in 10 mM trifluoracetic acid (TFA). Fractions were checked by scintillation counting, which revealed two major radioactive peptides, denoted A and B, accounting for 50% of the eluted radioactivity. The peptide pool was lyophilized, redissolved in 10 mM TFA, 6M guanidinium chloride and separated on a Vydac CI8 column using a 20–30% acetonitrile gradient in 10 mM TFA. Each peptide was further purified to homogeneity on the same column by applying an acetonitrile gradient in 20 mM ammonium acetate at pH 6.5, and the solutions evaporated to dryness. Their specific radioactivities were consistent with only one labelled site per molecule.

The two peptides were sequenced by automated Edman degradation. A portion of the sequenator effluent was diverted for monitoring of radioactivity. The results are shown in FIG. 1. Up to cycle 15, the sequences proved to be identical and correspond unequivocally to residues 118–132 of mature S1. In both peptides radioactivity was associated with an unidentified amino acid released at cycle 12, corresponding to position 129 in mature S1. No radioactivity was detected at cycles beyond 15. Thus it was established that GLU$^{129}$ was the site of crosslinking, and is therefore likely to be an important component of the nicotinamide interaction site.

EXAMPLE V

This Example illustrates the preparation of *B. pertussis* chromosomal DNA.

Two liters of *B. pertussis* (strain 10536) were grown in modified Stainer-Scholte medium as 16×125 ml aliquots using a 4 ml inoculum of saturated growth for each flask. This medium consists of L-proline 5 g/L, NaCl 2.5 g/L, $KH_2PO_4$ 0.5 g/L, KCl 0.2 g/L, $MgCl_2.6H_2O$ 0.1 g/L, Tris 1.5 g/L, casamino acids 10 g/L, methyl-β-cyclodextrim 2 g/L, $CaCl_2.2H_2O$ 0.02 g/L, mono-sodium glutamate 10 g/L, L-cysteine 0.004%, $FeSO_4.7H_2O$ 0.001%, niacin 0.004%, glutathione 0.015%, and asorbic acid 0.04%, pH.7.6. Samples were grown in 500 ml flasks, on a shaker at 35°–36° C., 150 rpm for 16.5 hr to log phase. The cells were spun in 500 ml aliquots at 5000 xg for 1 hr at 4° C. Each aliquot was washed with 25 ml TE buffer (10 mM Tris-HCl, 1 mM EDTA, pH 7.5,) then resuspended in 20 ml TE and frozen at −70° C. One pellet was resuspended in 90 ml TE and pronase added to 500 μg/ml. SDS was added to 1% and the sample incubated at 37° C. for 21.5 hr generating a clear lysate. The lysate was extracted with 1 volume of phenol saturated Tris-HCl at pH 7.5 at room temperature for 2 hr, with gentle agitation. The phases were separated by centrifugation at 2800 xg for 15 min at 20° C. and the aqueous phase extracted similarly with 1 volume of 1:1 phenol:chloroform. The phases were separated by centrifugation at 2100 xg for 10 min at 20° C. and the aqueous phase extracted with chloroform for 2 hr as described. The phases were separated by centrifugation at 1600 xg for 5 min at 20° C. and the aqueous phase subjected to dialysis at 4° C. against 2 L of 1M NaCl for 24 hr with one change of buffer, then against 2 L TE for 48 hr with one change of buffer.

EXAMPLE VI

This Example illustrates the generation of *B. pertussis* gene libraries.

1) λ gt11 EcoR I library

B. pertussis DNA (10 μg) was digested with EcoR I (10 units) in the presence of 100 mM Tris-HCl pH 7.5, 50 mM NaCl, 5 mM MgCl$_2$, 100 μg/ml BSA, 1 μg/ml RNAse A for various lengths of time in order to generate a set of partially digested DNA fragments. At each time point of 0.25, 0.5, 1, 2, 4 and 8 hrs, the sample was placed at 0° C. and EDTA added to 20 mM to stop the reaction. The samples were pooled and separated on a 10–40% sucrose gradient in TNE (20 mM Tris-HCl, pH 8.0, 5 mM EDTA, 1M NaCl) at 85,000 xg for 20 hr at 20° C. The gradient was fractionated from the top as 24 aliquots (0.5 ml) to which 1 ml aliquots of absolute ethanol were added to precipitate the DNA. The samples were incubated on dry ice for 30 min then centrifuged at 12,000 xg for 5 min at 4° C. The pellets were washed with 750 μl of 70% ethanol, incubated on dry ice for 5 min, centrifuged at 12,000 xg for 5 min, then dried. Each pellet was resuspended in 25 μl of sterile water and 5 μl aliquots of every alternate fraction were submitted to agarose gel electrophoresis to determine the size of the fragments. Samples containing DNA ranging in size from approximately 0.5 kb to 9 kb were pooled. The pooled EcoR I-digested B. pertussis DNA (0.4 μg) was ligated with EcoR I-digested, dephosphorylated λ gt11 DNA (0.5 μg) and was packaged into phage particles using a commercial kit. The phage library was propagated in E. coli Y1090 cells and was titred at approximately $10^{10}$ plaque-forming units(pfu)/μg of λ gt11 DNA. The library was amplified to $4 \times 10^{10}$ pfu/ml for screening clones. The amplification was performed on plates by growing cells to saturation overnight in media containing 0.2% maltose, then adding $10^4$ to $10^5$ pfu of library per 0.6 ml of cells and allowing the phage to adsorb to the cells for 15 min at 37° C. The sample was mixed with soft agar, plated, and incubated overnight at 37° C. The soft agar/cells/phage layer was scraped from the confluent plates which were washed with 4 ml SMG buffer (0.4M NaCl, 10 mM MgSO$_4$, 50 mM Tris-HCl, pH 7.5, 0.01% gelatin). The wash and phage agar were combined, 100 μl of chloroform added, and the mixture incubated at 37° C. for 15 min with gentle agitation. The sample was centrifuged at 4000 xg at 4° C. for 10 min twice to obtain a clear supernatant. Chloroform was added to a final concentration of 0.3% and the library stored at 4° C.

2) λ Charon 35 Sau3A I library

B. pertussis DNA (3 × 166 ug) was digested with Sau3A I (3 × 220 units) in the presence of 10 mM Tris-HCl pH 7.5, 100 mM NaCl, 10 mM MgCl2, 100 μg/ml BSA for 1 min, 2 min, or 3 min in order to generate very large fragments of DNA. After each reaction, EDTA was added to 20 mM and then 2.5 volumes of absolute ethanol added to precipitate the DNA as described above. The DNA was resuspended in TNE and separated on a 10–30% sucrose in gradient in TNE as described above. Fractions were taken as before and the DNA fragment sizes visualized by agarose gel electrophoresis. λ Charon 35 DNA (2 × 50 μg) was ligated to generate a circularized form before being digested with BamH I (2 × 20 units) in the presence of 150 mM NaCl, 6 mM Tris-HCl pH 7.9, 6 mM MgCl$_2$, 100 μg/ml BSA to remove the stuffer fragments. The lambda arms were purified by pelleting through an 8–20% potassium acetate gradient at 85,000 xg, for 16 hr at 32° C. The Sau3A I digested DNA was ligated with the lambda arms at 6° C. for 72 hr, then packaged into phage using a commercial kit. The phage library was propagated in E. coli LE392 cells and was titred at approximately $1 \times 10^5$ pfu/μg of lambda arms. The library was amplified to $1-2 \times 10^{10}$ pfu/ml for screening as described above.

EXAMPLE VII

This Example illustrates the screening of the B. pertussis libraries.

λ gt11 genomic library

A 30-base oligonucleotide probe was synthesized based on the nucleotide sequence of the gene encoding PT subunit S4. The DNA was purified from urea/acrylamide gels by uv-imaging and anion exchange chromatography on Whatman cellulose DE52. The sequence of the oligonucelotide was 5'GTAGCCAT-GAAGCCGTATGAAGTCACCCCG3', coding for amino acids 16-25 of the mature S4 protein. The oligonucleotide was 5' end-labelled in a reaction mix containing 10 ug DNA, 25 uCi [α-=P]ATP, 4 units polynucleotide kinase in the presence of 50 mM Tris-HCl, pH 9.5, 10 mM MgCl2, 5 mM DTT, 5% glycerol by incubation at 37° C. for 15 min. ATP was added to 1.5 mM and the incubation continued for 1.75 hr at 37° C. 10 ug of tRNA were added as carrier and the labelled DNA was separated from free ATP on a Sephadex G50 superfine column eluted with 0.1M triethylammonium bicarbonate, pH 7.6. Peak fractions were pooled and lyophilized to dryness. The pellet was washed with sterile water, relyophilized then resuspended at approximately 0.1 μg/ul.

Aliquots of the λ gt11 B. pertussis genomic library were plated on a Y1090 lawn on NZCYM plates containing 0.2% maltose. Plaque-lifts were made onto nitrocellulose filters which were sequentially treated with denaturing solution (1.5M NaCl, 0.5M NaOH) for 1 min, neutralizing solution (1.5M NaCl, 0.5M Tris-HCl pH 8.0) for 5 min, and rinsed briefly in 2xSSPE (0.36M NaCl, 20 mM sodium phosphate, pH 7.4, 2 mM EDTA) before being baked at 80° C. under vacuum for 2 hr to fix the DNA. Nitrocellulose filters were subsequently incubated in a prehybridization buffer comprising 5xSSC (0.75M NaCl, 75 mM sodium citrate, pH 7.5), 5 × Denhardt's mixture (0.1% Ficoll 400, 0.1% polyvinylpyrrolidone, 0.1% BSA), 0.1% SDS, 100 μg/ml herring sperm DNA for 2 hr at 45° C. The prehybridization buffer was removed and fresh buffer containing $10^7$ cpm of [$^{32}$p]-labelled oligonucleotide probe was added. Hybridization was carried out at 45° C. for 16 hr. The radioactive solution was removed and the filters rinsed briefly twice at room temperature with 5xSSC, 0.1% SDS to remove unbound probe. The filters were further washed twice with 5xSSC, 0.1% SDS for 1 hr at 50° C. then air-dried and subjected to autoradiography.

The plaque-containing plates were aligned with their autoradiograms and putative positive plaques were subjected to another two rounds of purification on plates. One clone (λ gt11-15-4-1) was chosen for detailed examination by Southern blot analysis.

2) λ Charon 35 genomic library

Aliquots of the λ Charon 35 B. pertussis genomic library were plated on an LE392 lawn on NZCYM plates containing 0.2% maltose. The plaque-lift, hybridization and washing protocols were performed as described. Positive plaques were purified twice more on plates and several clones, λ Ch 35 111, 121, 411, 421 and 431, were examined by Southern blot analysis. Example VIII:

This Example illustrates the analysis of the genomic clones.

1) Preparation of phage DNA

One liter (2×500 ml) of phage culture was prepared. LE392 or Y1090 cells were grown overnight in medium containing 0.2% maltose. Cells ($10^{10}$) were spun down at 4400 xg for 5 min at 4° C. and the pellet resuspended in 1 ml SMG buffer. Phage stock ($1.2 \times 10^8$ pfu) was added to the mixture and incubated at 37° C. for 15 min to absorb the phage to the cells. The phage/cell mixture was inoculated into 500 ml of medium and the culture shaken vigorously at 37° C. until lysis began (4-4.5 hr). Chloroform (10 ml) was added and shaking continued at 37° C. for an additional 15 min to complete the lysis. The sample was cooled to room temperature and DNase I and DNase-free RNase A (1 μg/ml each) were added for 30 min at room temperature. The cell debris was pelleted at 3500 xg for 20 min, then 29.2 g NaCl and 50 g polyethylene glycol (PEG 6000) were added to 500 ml of supernatant. The sample was gently agitated at room temperature to dissolve the solids, then incubated at 0° C. for 1-2 hr to precipitate the phage. The phage were harvested by centrifuging at 4400 xg at 4° C. for 20 min and were resuspended in 8 ml TM buffer (50 mM Tris-HCl, pH 7.5, 10 mM MgSO$_4$). Extraction with 8 ml chloroform to remove the PEG gave a clear supernatant which was applied to a step gradient of 5% and 40% glycerol in TM buffer and centrifuged at 154,000 xg at 4° C. for 1 hr. The supernatant was discarded leaving a phage pellet which was resuspended in 0.5 ml TM buffer. DNase I was added to 5 μg/ml and RNase A to 50 ug/ml and the sample incubated at 37° C. for 30 min. EDTA was added to 20 mM, pronase to 0.5 mg/ml, SDS to 0.5%, and the sample further incubated at 37° C. for 1 hr. The sample was gently extracted once each with phenol, phenol:chloroform 1:1, and chloroform and the phage DNA precipitated with ethanol.

2) Results

Clone 15-4-1 which was derived from the EcoR I gt11 library, was found by Southern blot analysis to contain the 4.6 kb EcoR I fragment encoding the entire TOX gene plus small 5'- and 3'-flanking regions.

The λ Charon 35 clones were found to be closely related. Some clones contained the entire TOX operon plus flanking regions in either orientation, and others did not include the entire TOX region.

The maps of clones 15-4-1, Ch 111, Ch 121/411, Ch 431 and Ch 421 are shown in FIG. 2.

EXAMPLE IX

This Example illustrates the construction of pUC-based plasmids containing the pertussis toxin operon (TOX) or portions thereof.

Phage DNA from the λ gt11 clone 15-4-1 was prepared as described and digested with restriction endonuclease EcoR I using standard methods. The DNA was purified by gel electrophoresis in low-melting-point agarose. The 4.6 kb band was identified by uv-illumination of the ethidium bromide stained gel and excised. The DNA was extracted by a freeze-thaw technique employing 0.3M sodium acetate, pH 7.0 and was precipitated with ethanol. DNA from pUC8:2, a derivative of pUC8 containing two extra restriction sites for Bgl II and Xba I in its multiple cloning site, was digested with EcoR I. The linearized DNA was dephosphorylated by standard methods using calf alkaline phosphatase (CAP), phenol extracted and precipitated with ethanol.

Figure 3:
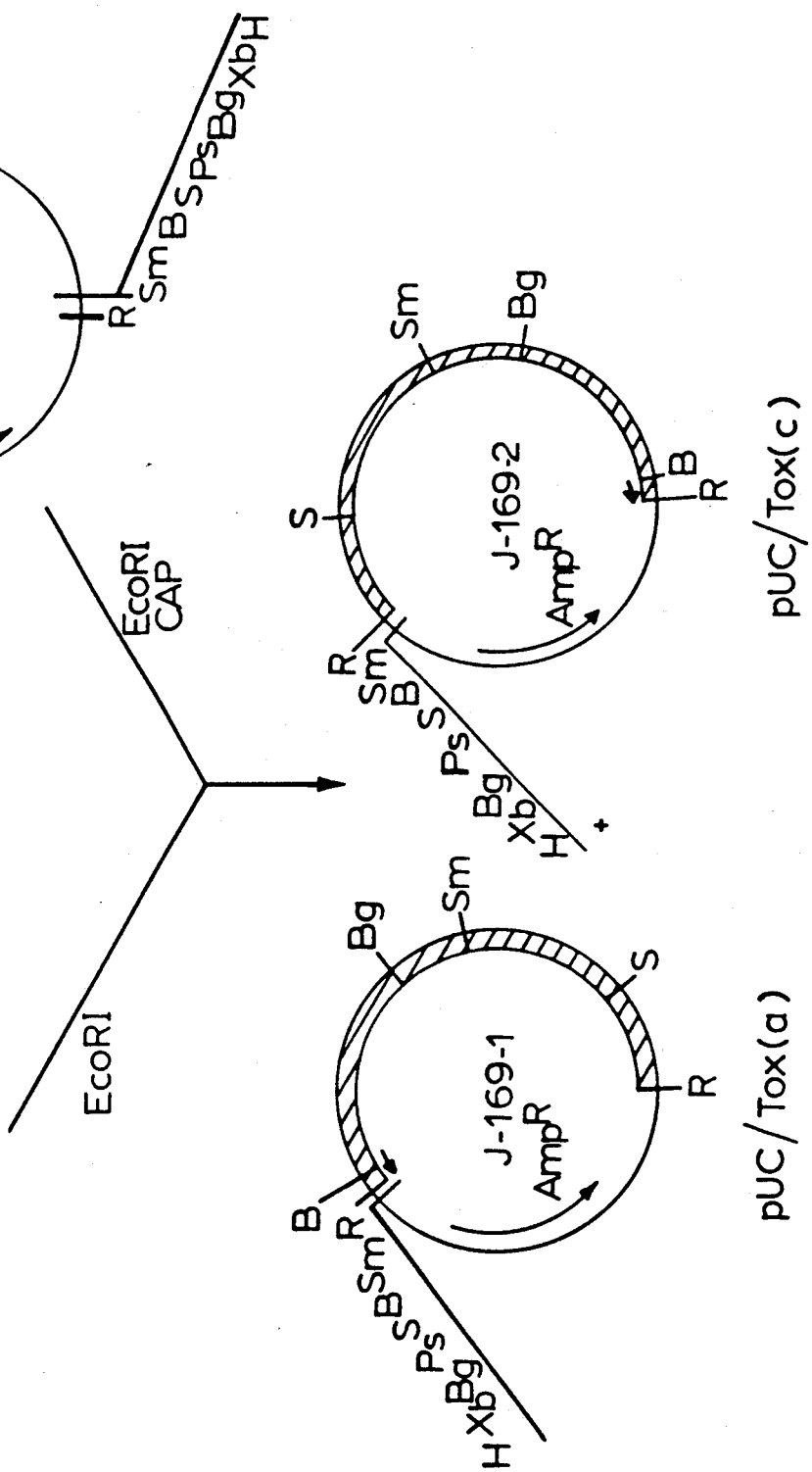
FIG. 3 shows the construction of subclones containing the TOX gene from the genomic clone λ gtII 15-4-1, with the TOX gene being inserted into the multiple cloning site of pUC8:2, which contains Bgl II and Xba I sites.
Figure 3:
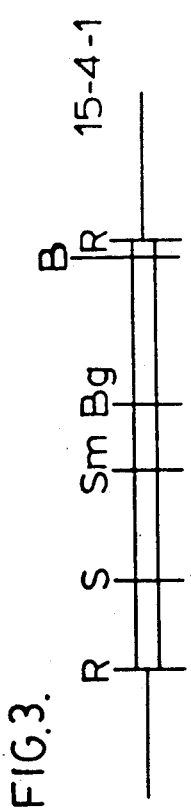

The pUC8:2-vector DNA and 15-4-1-derived-TOX DNA were ligated in a standard reaction and the ligation mixture used to transform competent JM109 cells according to standard procedures. The resulting colonies were analysed by a rapid DNA screening technique and two clones were chosen for large-scale preparation of plasmid DNA. These clones, J-169-1 and J-169-2, differed only in the orientation of the TOX insert. The construction of these clones is illustrated in FIG. 3. A deposit of plasmid J-169-1 was made with ATCC on Nov. 23, 1988 under accession number 40518.

EXAMPLE X

This Example illustrates the sequencing of the TOX operon.

1) Clones used

Figure 4A:
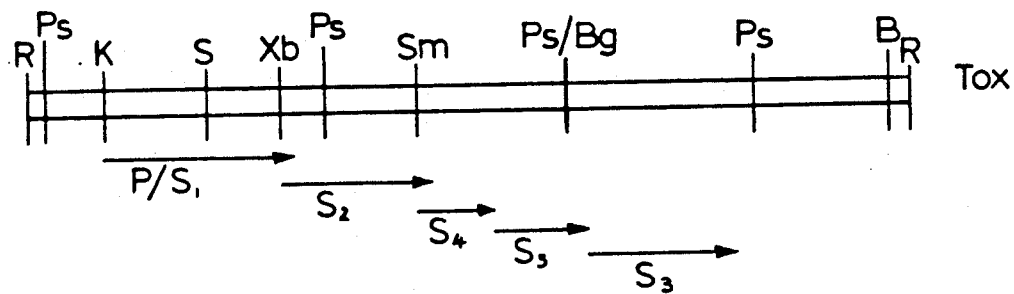
FIG. 4 shows the construction of subclones of the TOX gene used for sequencing the operon. In (A), a restriction map of the TOX gene and the protein subunits are indicated, with clones being derived from the pUC8:2/TOX clone J-169-1, and the subunit genes being subcloned into M13mp18, M13mp19 or pUC8:2, as indicated; in (B), clones of the 5' region of pUC8:2, S1 in M13mp18 and S1 in M13mp19 clones are described; in (C), clones of S2 in M13mp18 and M13mp19 is shown; in (D), clones of S4/S5 in M13mp18 and M13mp19 are shown; and, in (E), clones of S3 and the 3' region in M13mp18 and pUC8:2.
Figure 4B:
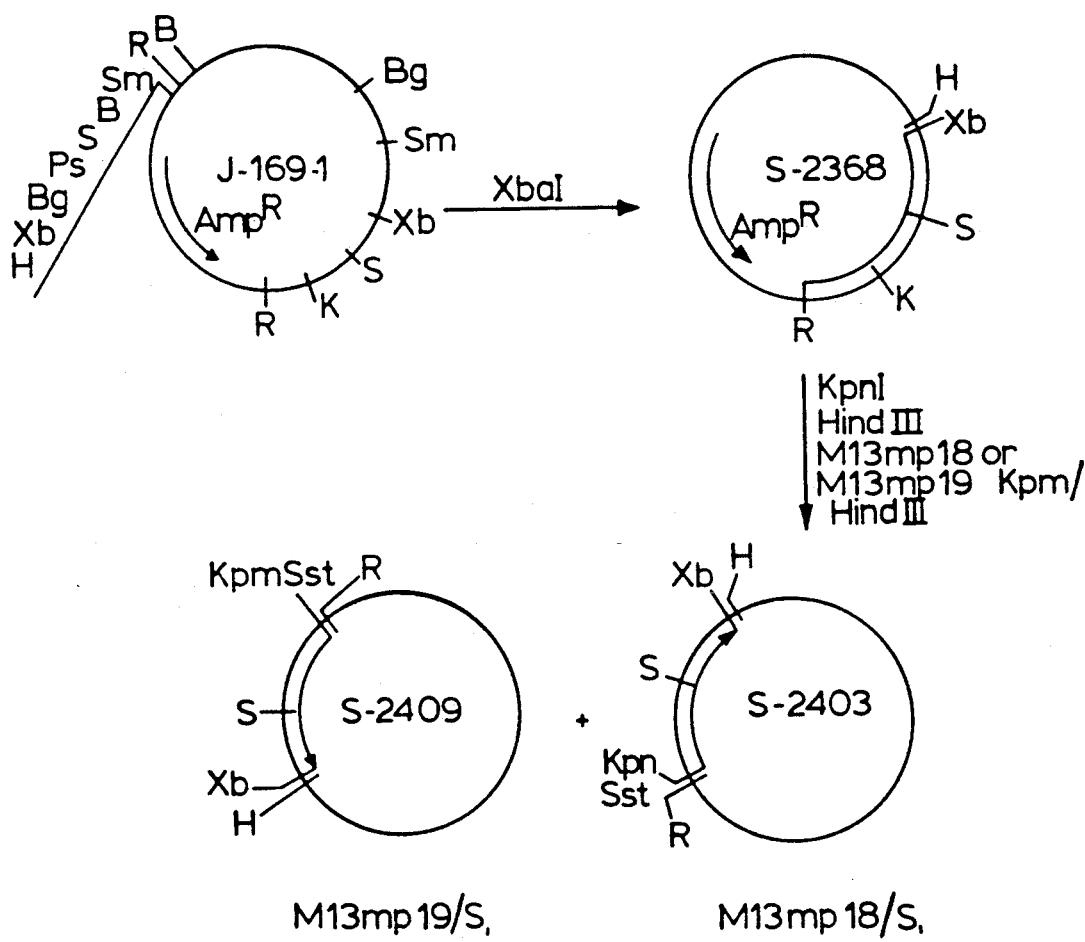
Figure 4C:
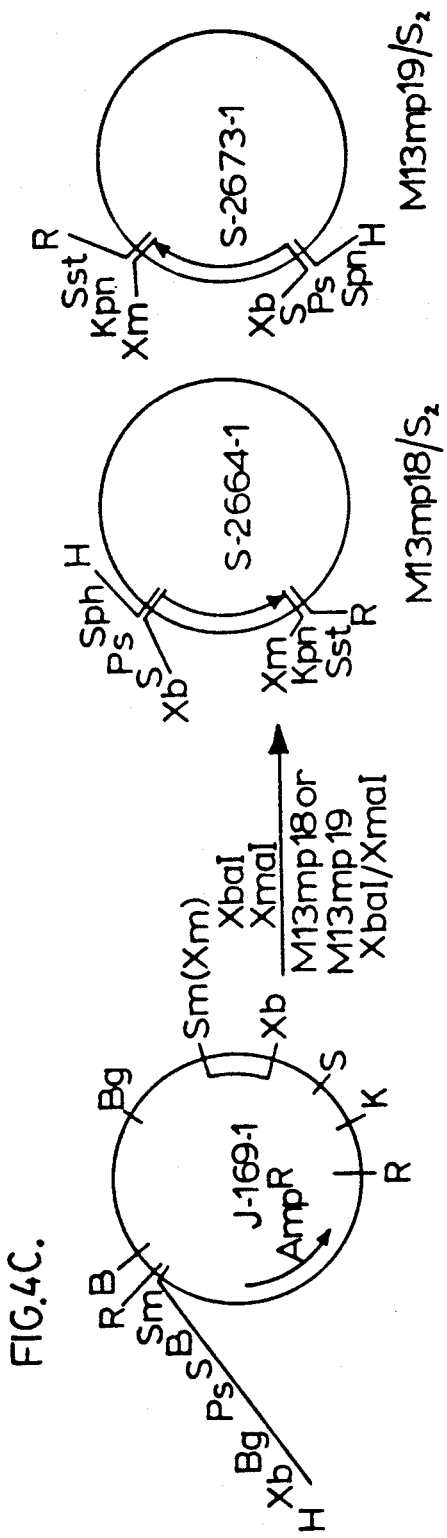
Figure 4D:
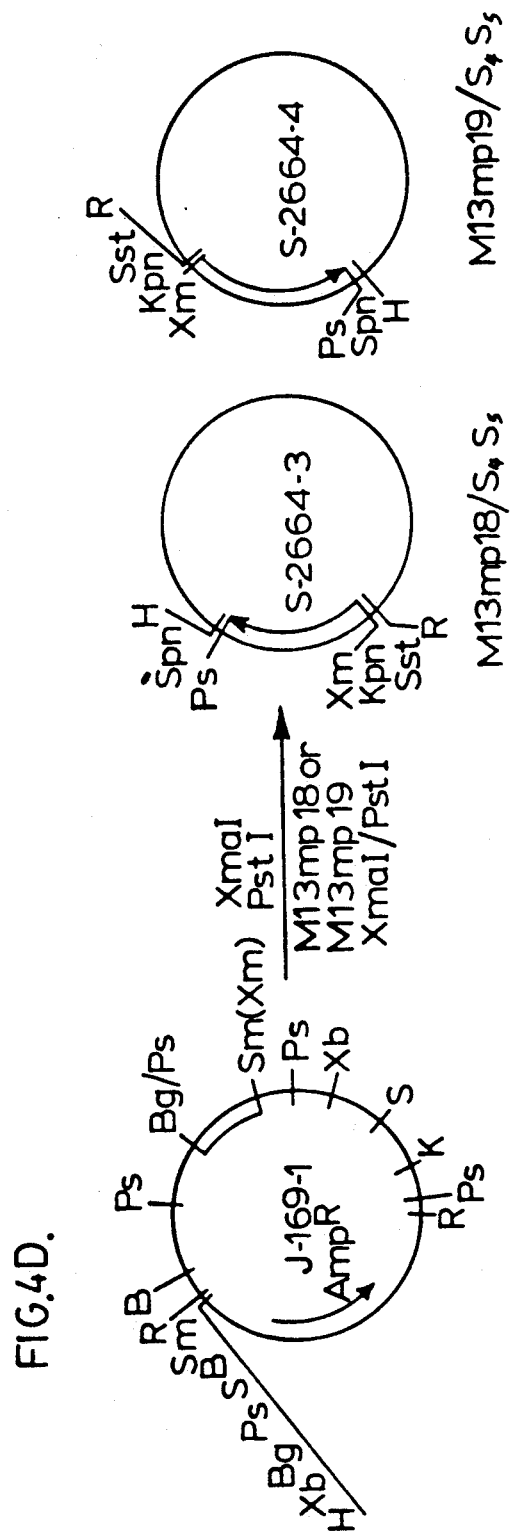
Figure 4E:
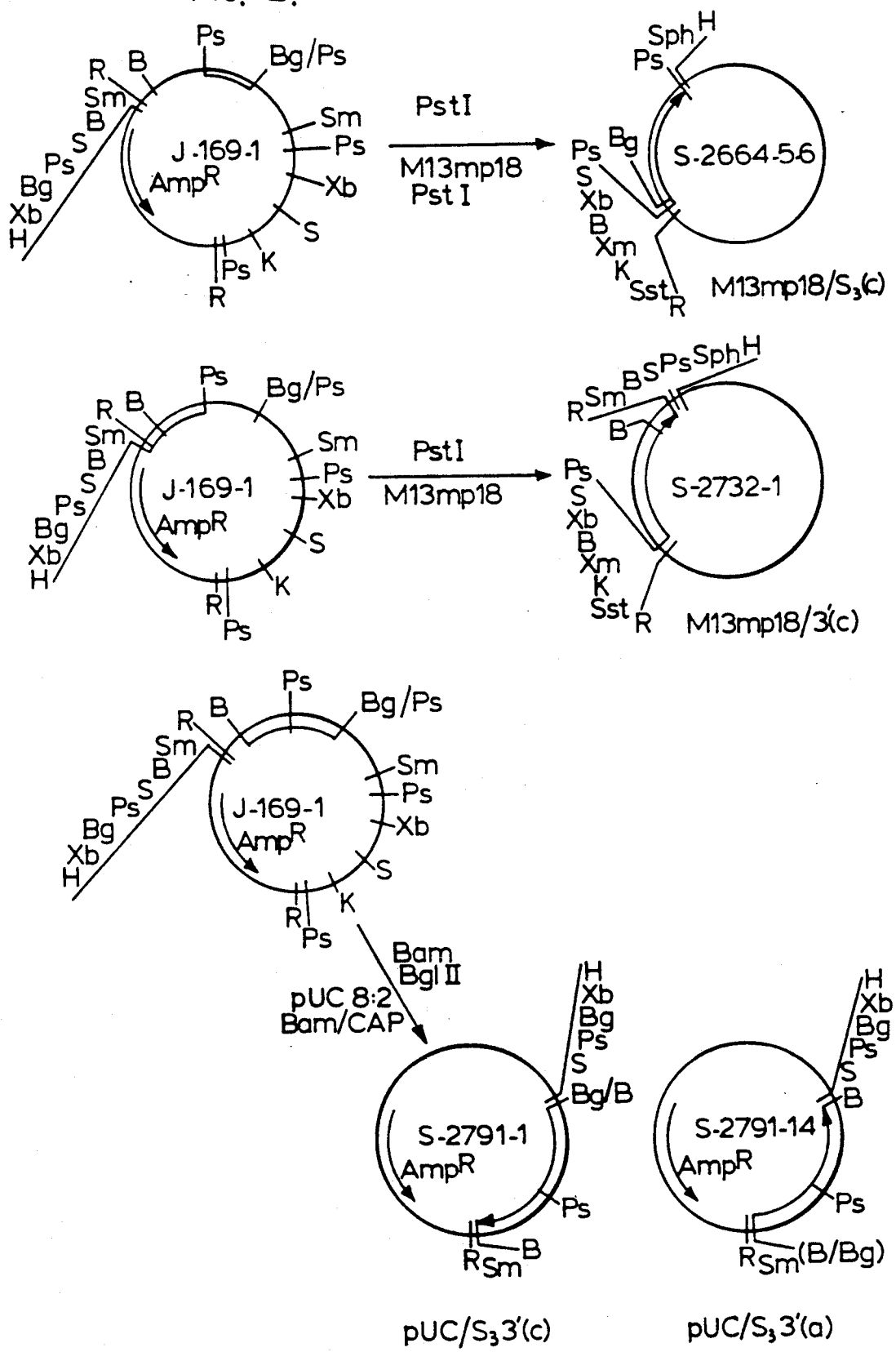
Figure 6A:
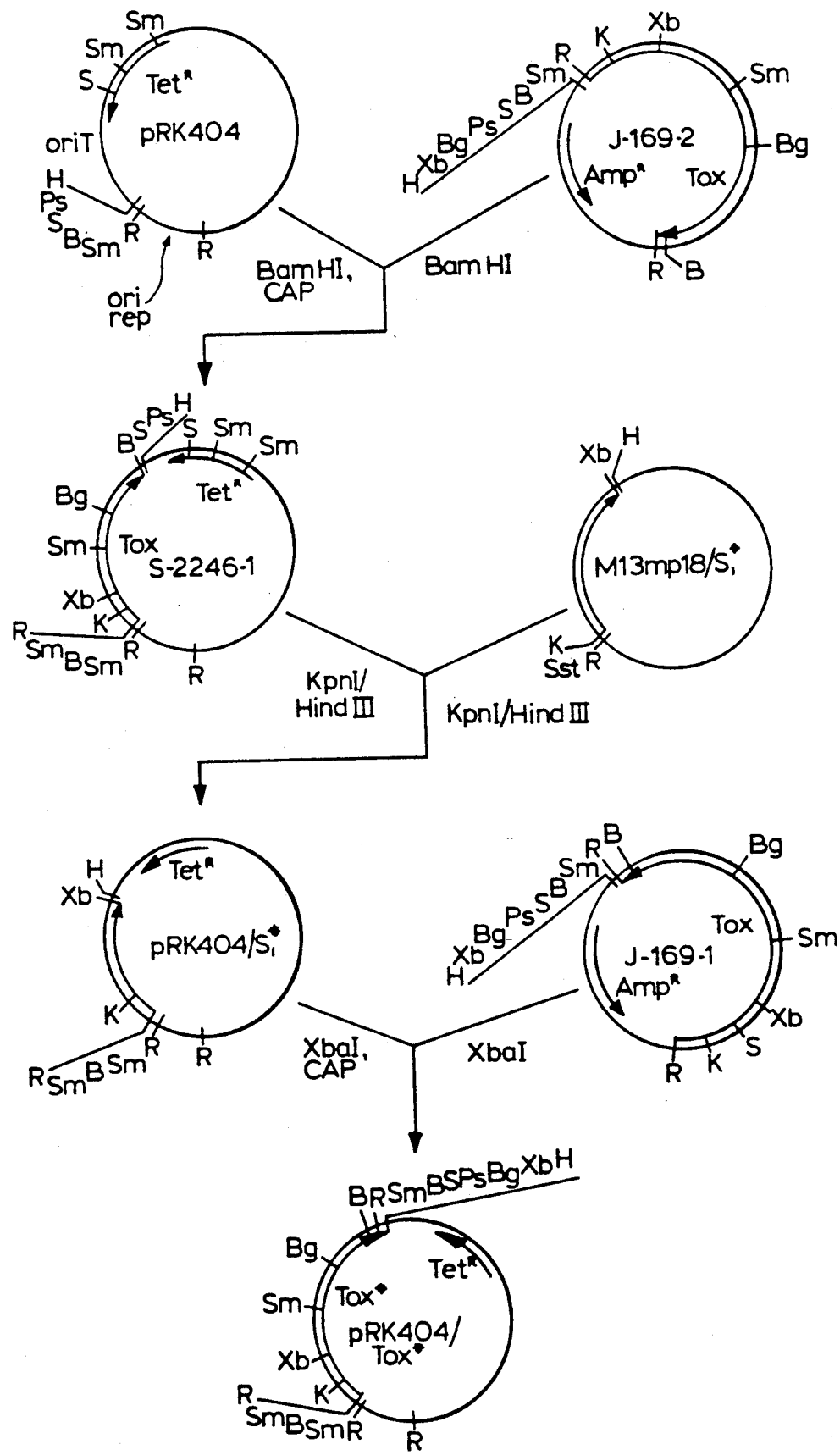
FIGS. 6A-D shows the construction of TOX or TOX analogue genes in the broad-host-range plasmid pRK404 (Ditta et al., Plasmid, 13, 149, [1985]). In (A) and (B), there is shown the construction of primary TOX analogue genes in pRK404 from mutated genes and native genes, while in (C), there is shown a typical construction of a "crossed" mutant from two S1-mutated genes.
Figure 6B:
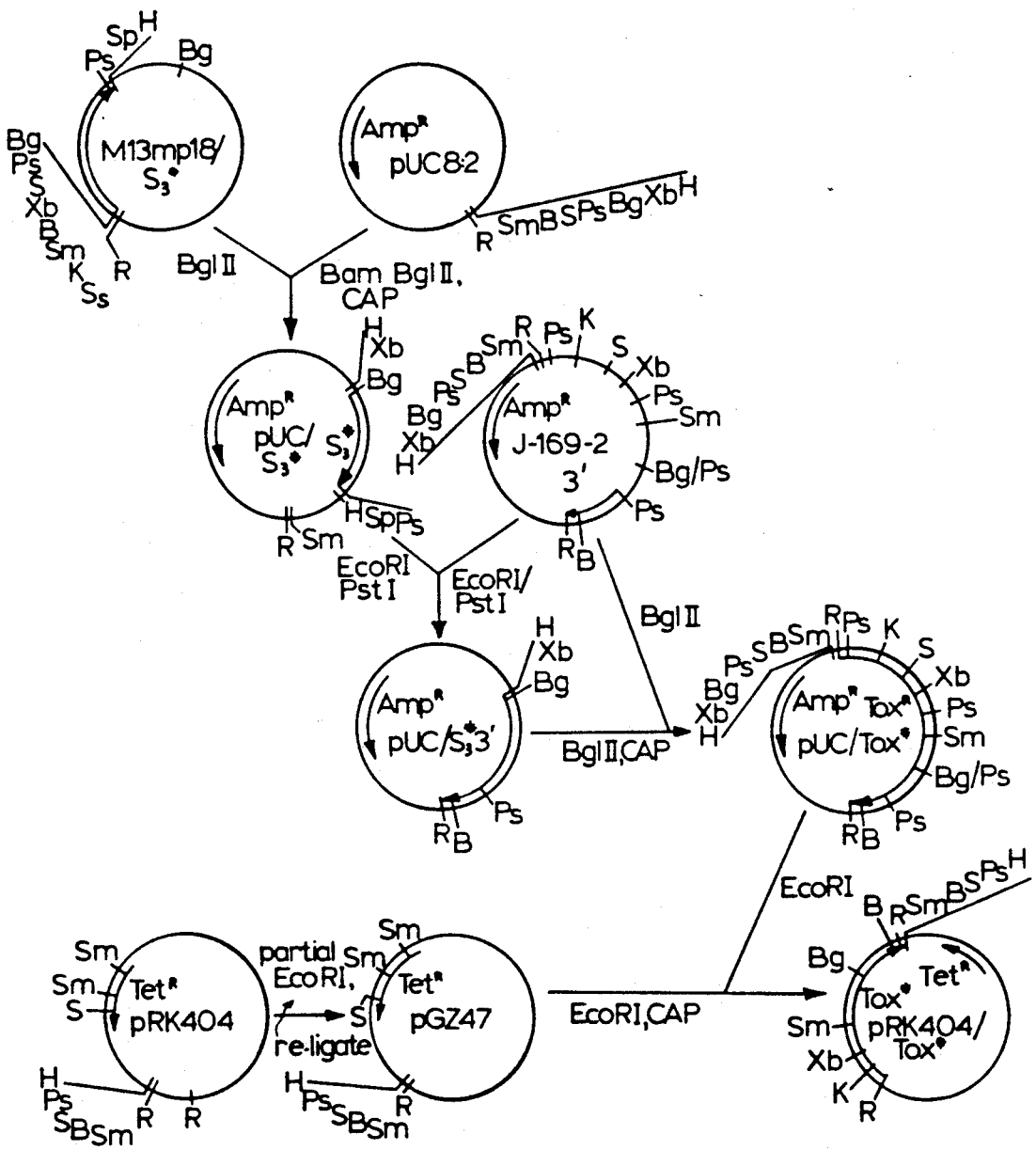
Figure 6C:
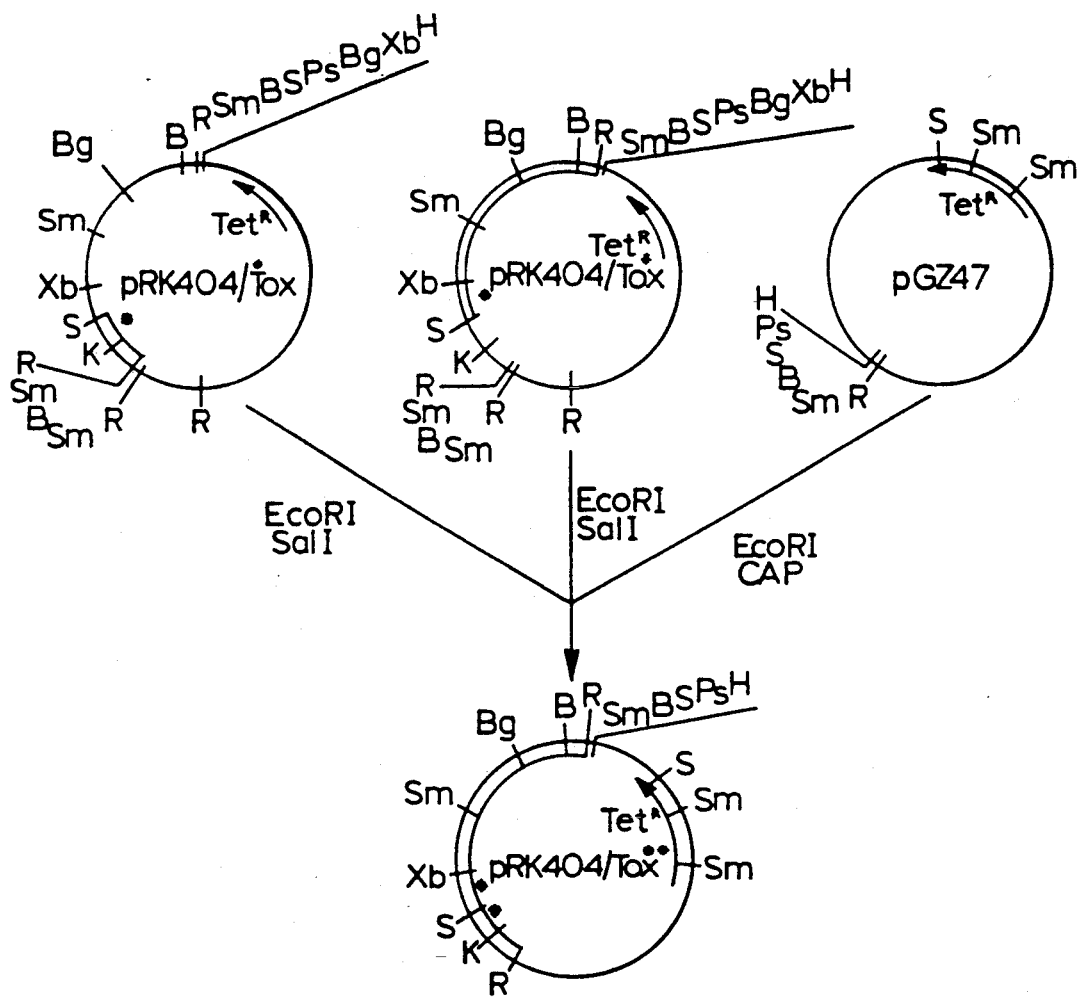
Figure 6D:
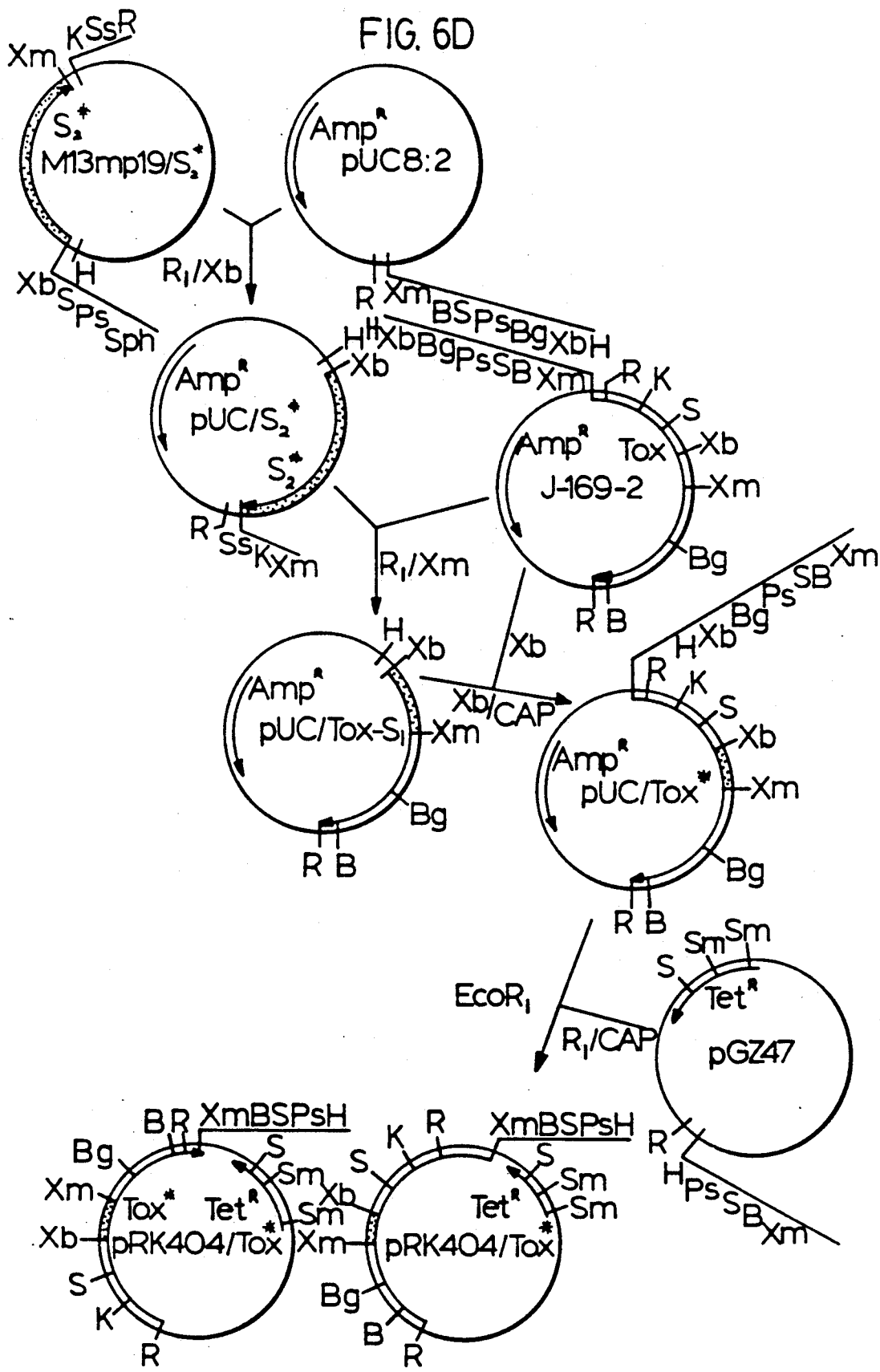

The clone J-169-1 was used as the source for all sequencing clones. The TOX operon was divided into five approximately equal DNA segments and was subcloned into M13 mp 18, M13 mp 19 or pUC8:2 as illustrated in FIGS. 4A, b, c, d and e.

2) Preparation of samples

M13 clones were maintained in JM101 and DNA for sequencing was prepared from single plagues on homogeneous plates. A saturated JM101 culture was diluted 1:50 with fresh medium and infected with a single plaque. The culture was grown with vigorous shaking at 37° C. for 6 hr. The cells were removed by centrifugation and the supernatant treated with ¼ volume of 20% PEG 6000, 2.5M NaCl to precipitate phage. The suspension was centrifuged and the phage pellet was resuspended in TE, then extracted gently twice each with phenol, phenol:chloroform (1:1) and chloroform. The phage DNA was precipitated with sodium acetate and ethanol, washed with 70% ethanol and dried. The DNA was resuspended in sterile water to a concentration of about 1 μg/ml for sequencing.

Sequencing primers of approximately 17-20 bases were synthesized on an ABI 380A DNA synthesizer using phosphoroamidite chemistry and were purified as described above.

3) Sequencing

The dideoxy chain termination method of Sanger was used for all sequencing reactions, employing either Klenow polymerase or Sequenase T7 enzyme.

4) Results

The entire TOX operon, as previously defined, was sequenced and the result compared with published sequences. There was excellent agreement with the TOX sequence of strain BP 165 reported by Nicosia et al., except for four base differences. The T at position 315 in the 5'-flanking region is unique to *B. pertussis* strain 10536. The three other substitutions are in the S1-coding region at positions 710, 1200 and 1202 resulting in two unique amino acids, GLU34 and VAL198. The nucleotide sequence and derived amino acid sequence are shown in FIG. 5.

EXAMPLE XI

This Example illustrates mutagenesis of the TOX gene.

1) Clones used

For mutations in the S1 gene, clone S-2403 (M13 mp18/S1) was used and for the mutations in the S3 gene, clone S-2664-5-6, (M13 mp18/S3 (c)) was used. These clones are represented in FIG. 4.

2) Mutagenesis protocol

Single-stranded DNA was prepared from phage stocks derived from single plaques on homogeneous plates as described previously. Mutagenic primers of appropriate sequence and length were synthesized on an ABI 380A DNA synthesizer.

Commercial kits based on the phosphorothioate procedure developed by Eckstein were used for in vitro mutagenesis. Briefly, the mutagenic oligonucleotide was annealed to the single-stranded (wild-type) template and polymerization carried out using as substrates a phosphorothioate dCTP analogue and natural dATP, dGTP and dTTP. The double-stranded DNA was nicked with Nci I and the native strand digested with exonuclease III beyond the point of the mutation. The complementary strand was protected from Nci I-nicking by the phosphorothioate groups. The complementary strand then served as a template in a second round of polymerization, to yield double-stranded DNA with the mutation in both strands. This DNA was amplified in E. coli, and the mutation confirmed by sequencing.

Thirty-five primary mutations were generated and an additional 14 were derived by constructing crosses among these. The mutation efficiency varied with the change desired. From one to six base changes and deletions of up to 15 consecutive bases were accomplished. The resulting amino acid changes are summarized in Table 1a.

EXAMPLE XII

This Example describes the construction of plasmids for expression of mutated TOX genes in B. parapertussis and characterization of the PT analogues produced.

1) Replicating plasmids

Replicative-form DNA from M13 clones was used to reconstruct the TOX operon containing the desired mutation in pRK404. pRK404 is a derivative of pRK290, a conjugating plasmid of the pRK2 family, incompatibility group P-1. It is 10.6 kb in size, carries a tetracycline resistance ($Tet^R$) gene, and has a multiple cloning site from pUC8. The construction schemes for reintegrating S1 and S3 primary mutations into the operon are shown in FIG. 6 and the resulting clones are indicated in Table 1a. Crossed mutations in S1 were generated using internal restriction sites, especially the unique in Sal I site. A general scheme for crossed mutations in S1 is also shown in FIG. 6 and the resulting clones are indicated in Table 1a.

2) Suicide plasmids

A conjugative but non-replicative plasmid was developed for random integration of TOX or mutated TOX into the chromosome of Bordetella species. FIG. 7 demonstrates the construction of these clones.

Plasmids of the types described in (1) and (2) above were introduced into B. pertussis by conjugation. The resulting strains were grown in shake-flasks or in a fermentor, and the culture supernatants were assayed as follows for concentration of toxin analogue by ELISA. Microtiter plates were coated with fetuin (2 μg/ml) in 0.05M potassium carbonate, pH 9.6 at 4° C. overnight in a humid environment. The plates were then wased twice with Delbecco's PBS containing 0.1% w/v Tween-20 and dried. Sample supernatants or wild-type PT were serially diluted and added to the wells, and the plates incubated for 30 min at room temperature then washed. Bound PT was detected using peroxidase-conjugated affinity-purified rabbit anti-PT antibodies.

Residual toxicity was measured by the CHO cell clustering assay, to determine the toxicity relative to native PT. Certain PT mutants were purified as described for native PT in Example I, and assayed for ADP-ribosyltransferase activity. These data are summarized in Table 1b. Expression of the S1 epitope recognized by MAb PS21 was assessed by a modified indirect ELISA on culture supernatants. Fetuin-bound PT analogues were reacted with PS21 as the first antibody and visualized with an enzyme-conjugated affinity-purified goat anti-mouse IgG as the second antibody. The presence or absence of the S1 epitope recognized by MAb PS21 is indicated in Table 1b.

EXAMPLE XIII

This Example illustrates the construction of plasmids for deletion and replacement of the endogenous B. pertussis TOX operon.

1) Plasmids containing TOX flanking regions a) 5'-flanking region

Figure 8A:
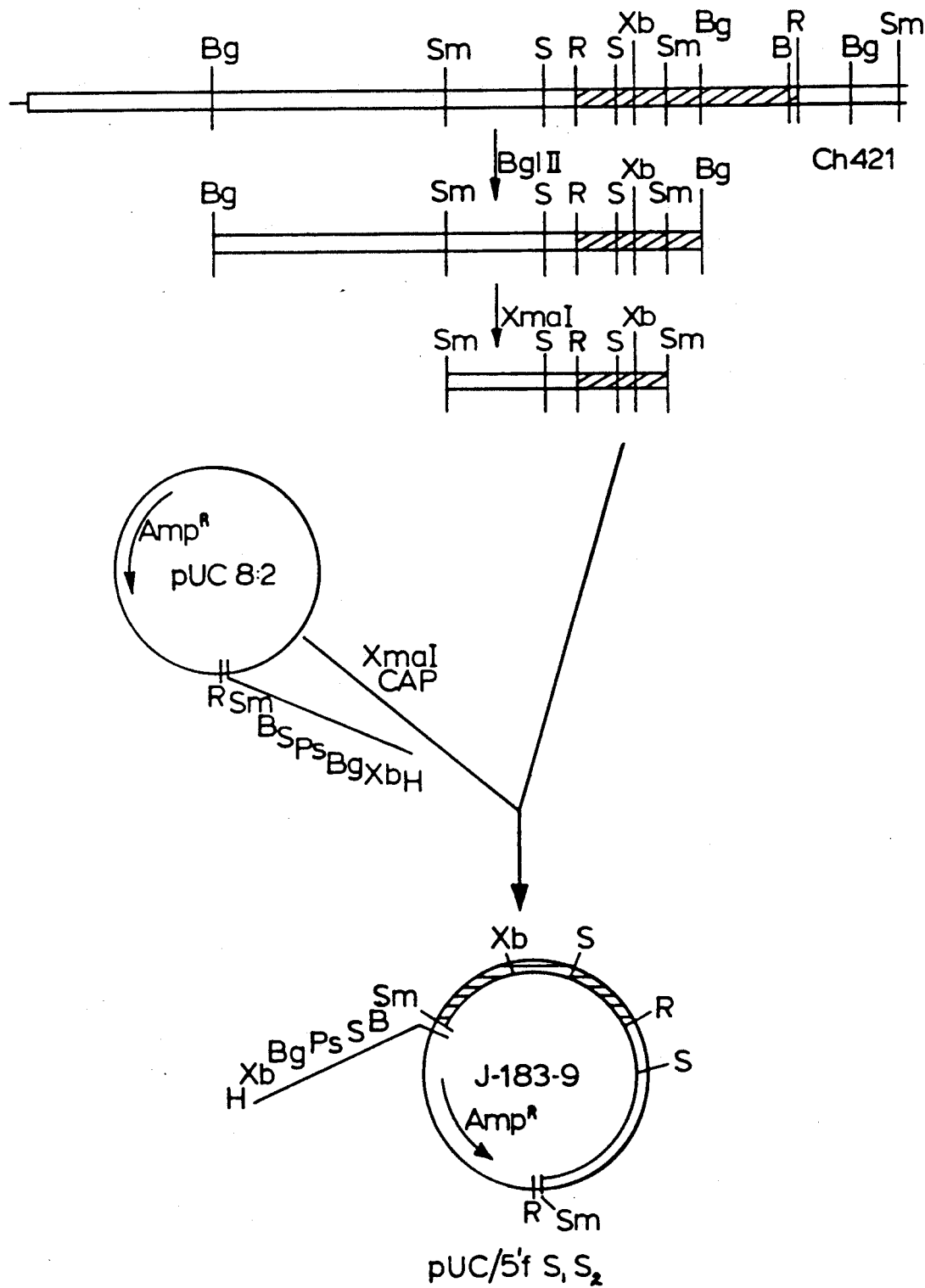
FIG. 8 shows the cloning of the 5'- and 3' flanking region of the TOX gene. (A) shows the construction of the 5' portion of TOX in pUC8:2 from the λ Charon 35 clone Ch421; (B) shows the construction of the 3' portion of TOX in pUC8:2 from λ Ch 111; and (C) shows the generation of a pUC8:2 clone containing TOX plus its 5'- and 3'-flanking regions.

The Ch 421 DNA was first digested with Bgl II and and 11 kb fragment was purified by agarose gel electrophoresis. The Bgl II fragment was digested with Xma I and the 5 kb band subcloned into pUC8:2 previously restricted with Xma I and dephosphorylated. JM109 cells were transformed with the ligation mixture to give colonies which were analysed by a rapid DNA screening method. The clone J-183-9 was found to contain approximately 2.9 kb of the 5'-flanking region, the TOX promoter and the genes for subunits S1 and S2. FIG. 8a shows the derivation of clone J-183-9.

b) 3'-flanking region

Figure 8B:
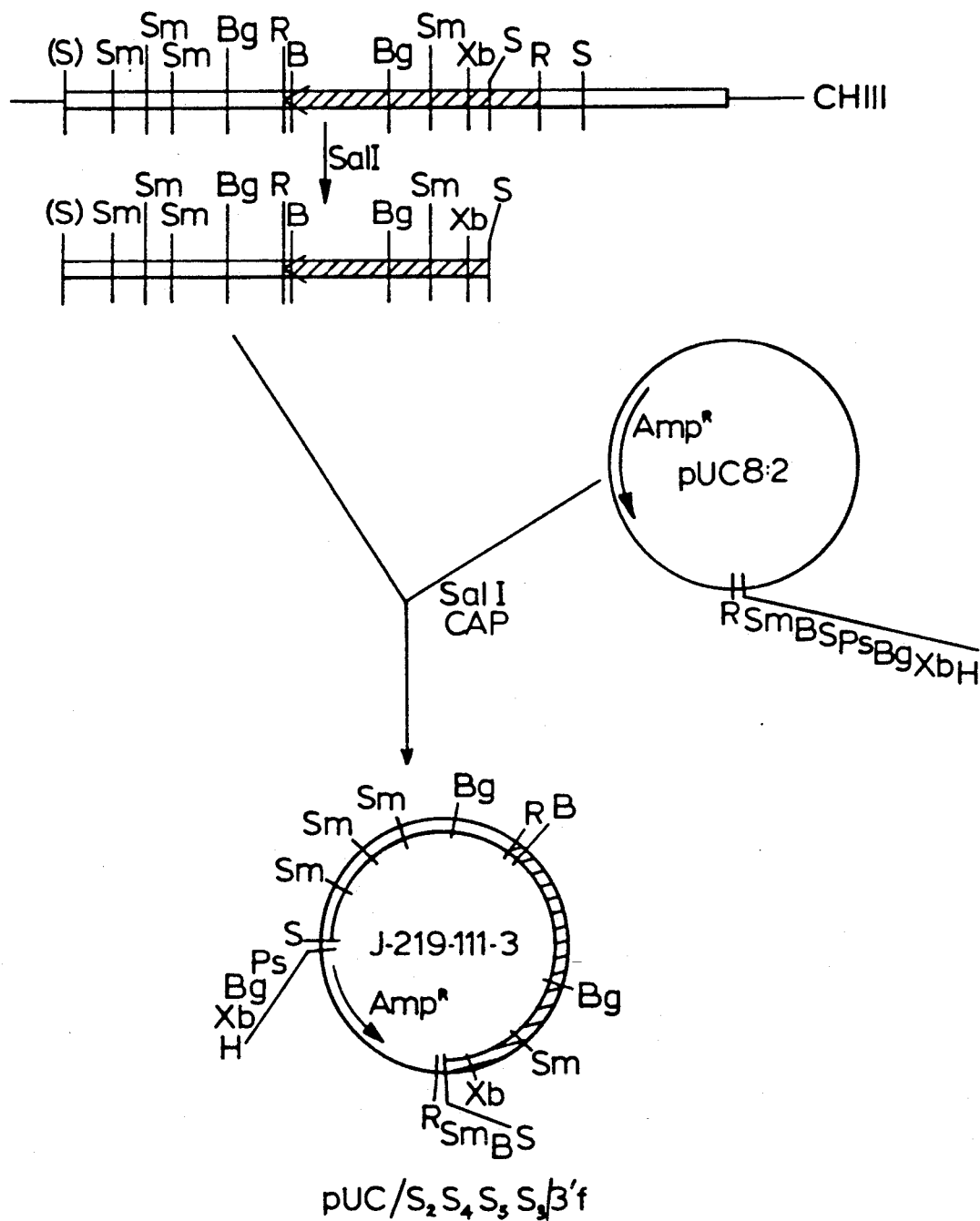

The Ch 111 DNa was digested with Sal I and an approximately 8 kb fragment of B. pertussis DNA was gel-purified. This DNA fragment was inserted into pUC8:2 previously digested with Sal I and dephosphorylated. JM109 transformants were screened and the clone J-219-111-3 was identified as containing part of the S1 gene, all of the remaining structural genes, and about 3.9 kb of the 3' flanking region. FIG. 8b shows the construction of this clone.

c) TOX gene with 5'- and 3'-flanking regions.

Figure 8C:
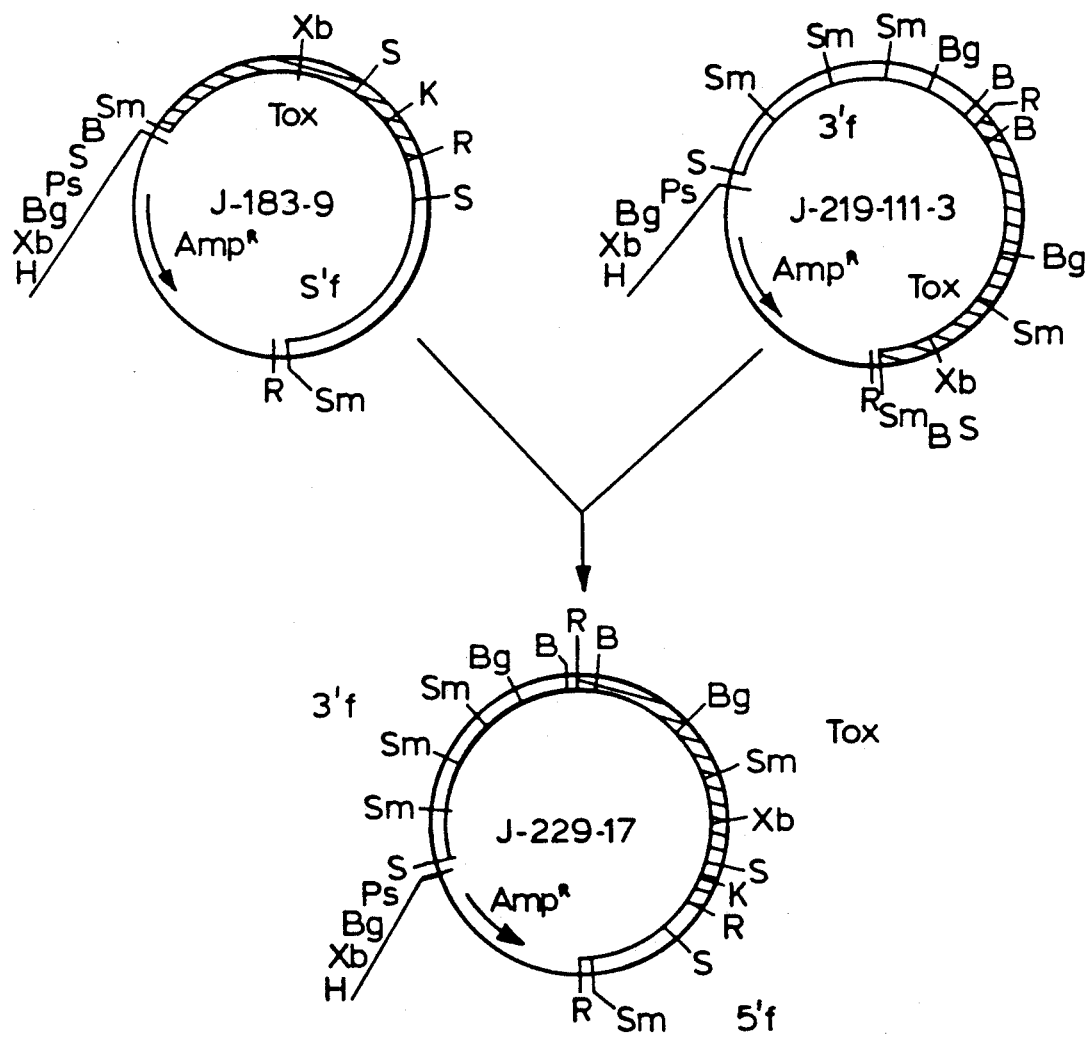

Clone J-183-9 was digested with Xba I and the approximately 7 kb fragment containing pUC8:2, the 5'-flanking region and the promoter region of the S1 gene was gel-purified and dephosphorylated. J-219-111-3 DNA was digested with Xba I and the approximately 8 kb fragment containing the structural genes for subunits S2 to S5 and the 3'-flanking regions was gel- purified. These DNA fragments were ligated and the JM109 transformants were screened to give clone J-229-17. This clone contains about 2.9 kb of the 5'-flanking sequence, the entire TOX operon, and about 4 kb of the 3'-flanking sequence. Its construction is illustrated in FIG. 8c.

2) TOX-deleting plasmids

Figure 9A:
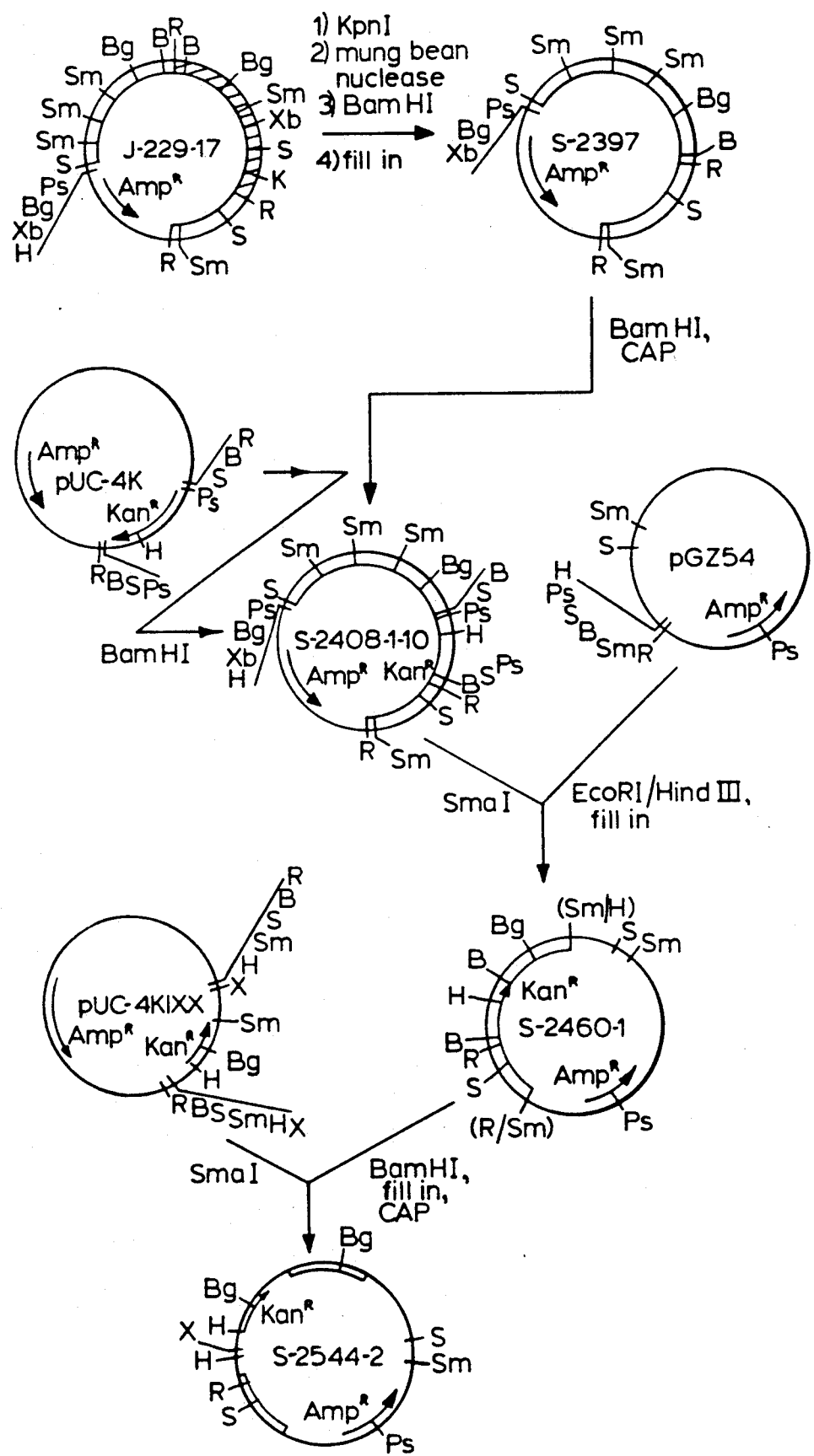
FIGS. 9A-C shows the construction of plasmids for the deletion of the TOX operon from the *B. pertussis* chromosome by homologous recombination.
Figure 9B:
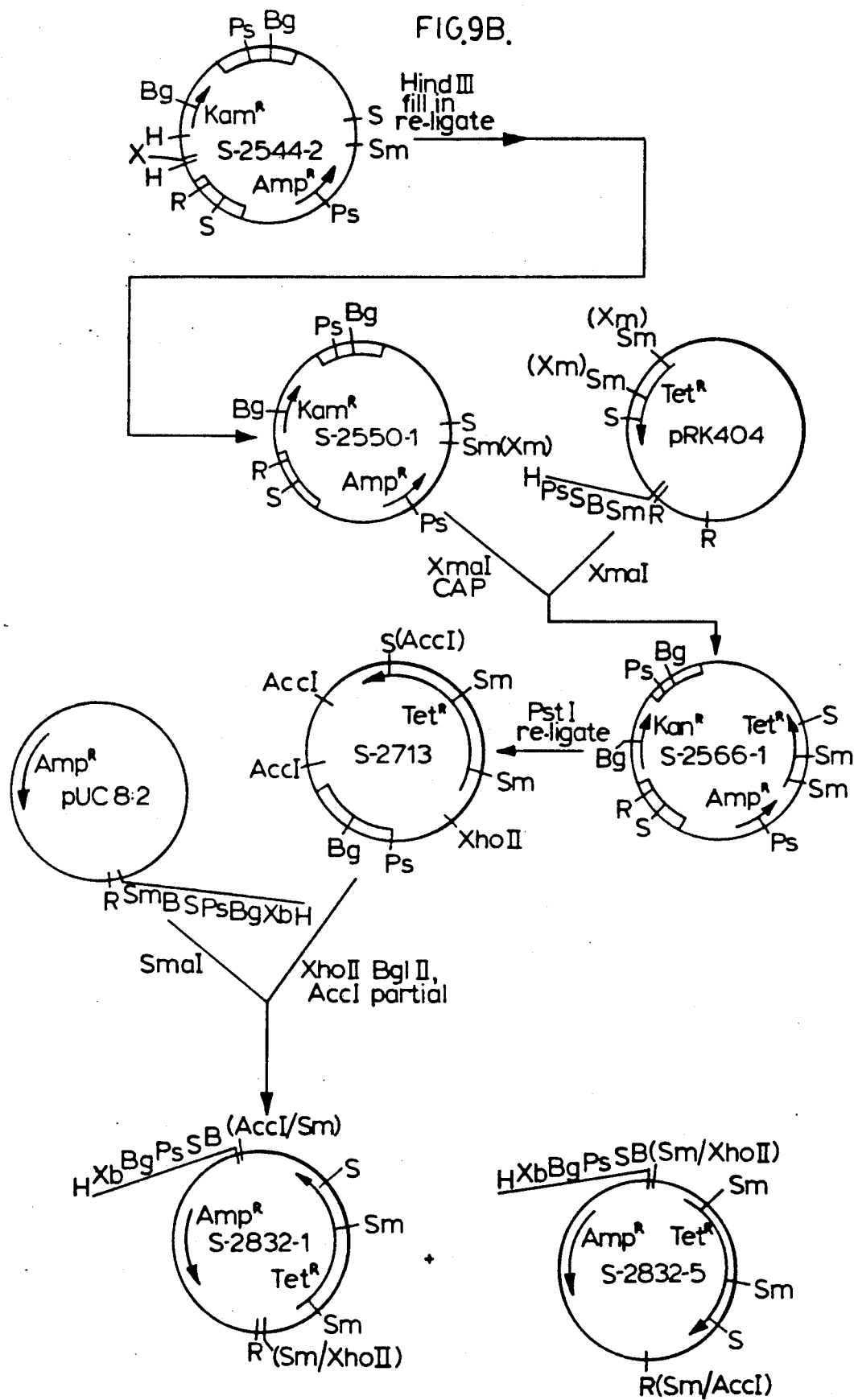
Figure 9C:
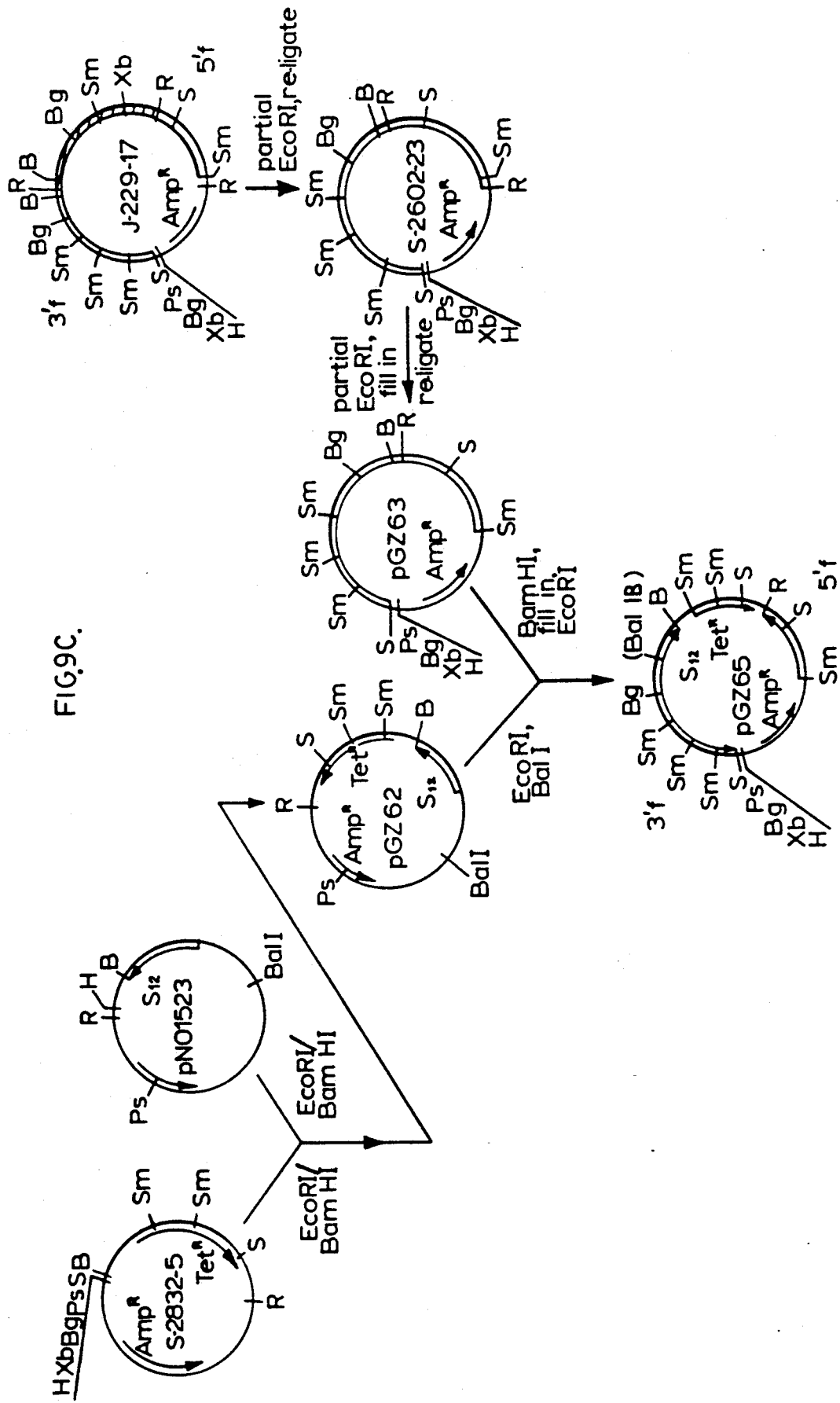

Plasmid pRK404 and its construction is shown in FIG. 9. The $Tet^R$ gene was cloned as an EcoR I/BamH I restriction fragment into plasmid pN01523 to generate pGZ62. Plasmid pGZ63 contains the 5'- and 3'-flanking regions without any intervening DNA. The S12-$Tet^R$ gene-sandwich from pGZ62 was cloned between the flanking regions of pGZ63 to produce plasmid pGZ65. The construction of these plasmids is summarized in FIG. 8d.

3) TOX-reintegrating plasmids

Figure 10:
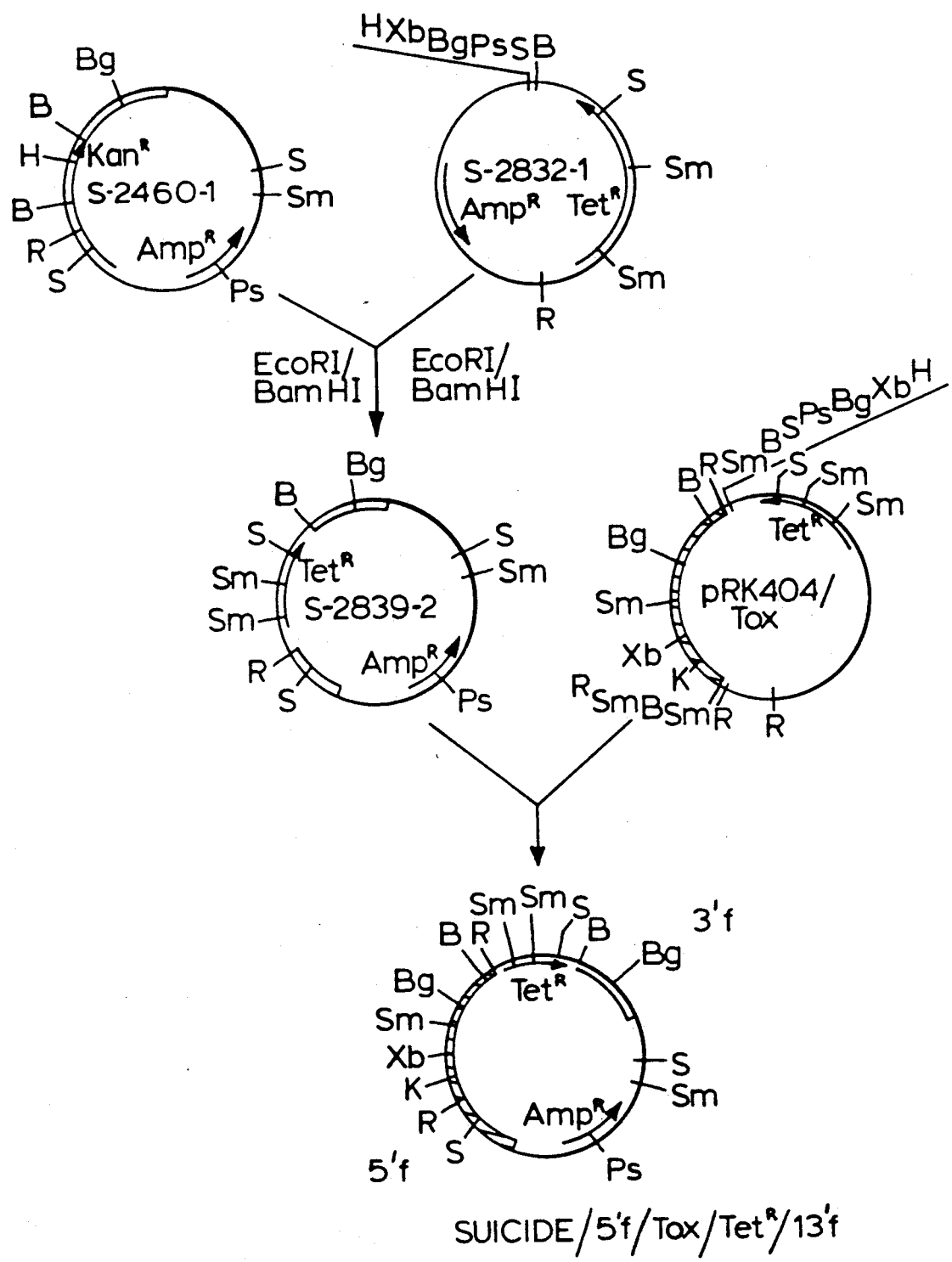
FIG. 10 shows the construction of plasmids for reintegration of TOX analogues into the *B. pertussis* genome by homologous recombination, the final plasmids being based on the suicide plasmid shown in FIG. 7 and containing the tetracycline resistance gene from pRK404 placed 3' to the TOX analogue gene.

To express mutated TOX genes in TOX⁻ strain of B. pertussis conjugative suicide plasmids of the type shown in FIG. 10 were constructed. They contain the TOX gene, extensive 5'- and 3'-flanking sequences and have a $Tet^R$ gene for selection cloned downstream from the TOX coding regions.

EXAMPLE XIV

This Example illustrates the deletion of the TOX gene from the B. pertussis chromosome and the reintegration of in vitro-mutated TOX genes.

1). Transformation of B. pertussis

Strains of B. pertussis were transformed by electroporation. Cells were grown in 100 ml of modified Stainer-Scholte medium to a density of about 10⁹ cells/ml, harvested in a clinical centrifuge (4000 xg for 15 min at 20° C.), washed in 25 ml of electroporation buffer (0.3M sucrose, 1 mM MgC12, 7 mM potassium phosphate, pH 7.2) and resuspended in 10 ml of the same. Plasmid DNA was added to 500 ul of the cell suspension and the mixture incubated on ice for 10 min. The cells were subjected to a single 25 kV/cm, 40 us exponential decay voltage pulse with a BTX Transfector 100, using a cuvette electrode with a 0.8 mm gap. Three ml of medium were added and the cells incubated with shaking at 37° C. for 60 min. The cells were harvested by centrifugation at 12,000 xg for 2 min, resuspended in 100 $\mu$l of medium, spread onto a Bordet-Gengou plate with antibiotic selection and incubated for 2-5 days at 37° C.

a) Deletion and replacement of the TOX operon

B. pertussis str29 is a spontaneous rpsL streptomycin resistant derivative of B. pertussis 10536. Plasmid pGZ65 contains a gene cartridge consisting of the pRK404 Tet$^R$ gene and the E. coli S12 gene cloned between the 5'- and 3'-flanking sequences of the TOX operon. This plasmid was linearized with Hind III and used to transform B. pertussis str29 to Tet$^R$, Str$^S$ resulting in the deletion of the TOX operon : by homologous recombination. This TOX-deleted strain was termed 29-8 and a Southern blot analysis demonstrated the excision of the TOX allele and its replacement by the Tc$^r$, S12 gene cartridge. This strain was deposited with ATCC on Nov. 30, 1989 under accession No. 53,973. To excise the S12-Tet$^R$ gene cartridge, strain 29-8 was subsequently transformed with linear pGZ63 plasmid DNA. Plasmid pGZ63 consists of the TOX 5'- and 3'-flanking sequences but contains no intervening DNA. Transformation with this plasmid resulted in the generation of B. pertussis 29-9 which is a streptomycin-resistant, TOX-deleted strain but contains no heterologous DNA inserted at the TOX locus. This strain was used as the host for expression of in vitro mutated TOX genes. Plasmids of the type shown in FIG. 10 contain a gene cartridge consisting of a mutated TOX gene and a Tet$^R$ gene. This gene cartridge was recombined into the B. pertussis 29-9 chromosome following introduction of the plasmid into the strain by conjugation or transformation. Expression of the TOX gene, toxicity of the PT analogues and maintenance of the S1 epitope recognised by MAb PS21 were determined as described before. The recombinant B. pertussis strains constructed and the properties of the secreted PT analogues are shown in Table 5.

EXAMPLE XV

This Example describes the in vivo testing of PT mutants in mice.

PT mutants were purified from culture supernatants and recombinant B. parapertussis strains as indicated in Example I. These proteins were injected into mice at three different doses to test the following characteristics, according to standard procedures: acute toxicity, histamine sensitization activity and potency in the mouse intracerebral challenge test. The results are presented in Table 2.

To test their immunogenicity, PT analogues were injected into female BALB/C mice, 9 to 11 weeks old, at doses of 2.0, 0.5 and 0.125 $\mu$g. Mice were pre-bled and immunized on day 0. On day 23 the mice were bled again and boosted with the same immunogen, and on day 37 the mice were bled again. Blood samples (0.4–0.5 ml/mouse) were collected by orbital sinus bleeding and the resulting sera stored at −20° C. to await testing. Sera were assayed for their ability to neutralize PT-induced CHO cell clustering (Table 3), and for specific antibody responses in antigen-coat, indirect ELISA (Table 4). As may be seen from Tables 3 and 4, PT analogues are capable of inducing neutralizing antibodies and anti-PT, anti-S1 and anti-B oligomer responses.

SUMMARY OF DISCLOSURE

In summary of this disclosure, the present invention provides a novel method of detoxifying pertussis by identification of specific functional sites of pertussis toxin and production of recombinant holotoxins by site-directed mutagenesis of the toxin gene. The resulting toxin analogues are detoxified, retain an immunodominant S1 epitope, are immunogenic and are protective against the disease pertussis. Modifications are possible within the scope of this invention.

TABLE 1a

Summary of Mutations introduced into Pertussis Toxin

| Mutation Number | Mutation | Clone No. |
|---|---|---|
| 1. | ARG$^9$ → $\Delta^9$ | S-2679-1-11 |
| 2. | ARG$^9$ → GLU$^9$ | S-2815-1-8 |
| 3. | ARG$^9$ → LYS$^9$ | S-2953-21 |
| 4. | ARG$^9$ → HIS$^9$ | S-3046-4 |
| 5. | ARG$^{13}$ → $\Delta^{13}$ | S-2679-2-1 |
| 6. | ARG$^{13}$ → GLU$^{13}$ | S-2779-2-1 |
| 7. | ARG$^9$-ARG$^{13}$ → $\Delta^{9-13}$ | S-2829-2-19 |
| 8. | ARG$^9$ ARG$^{13}$ → GLU$^9$ GLU$^{13}$ | S-2779-3-2- |
| 9. | ARG$^{58}$ → GLU$^{58}$ | J-444-2-2 |
| 10. | ARG$^{57}$ ARG$^{58}$ → $\Delta^{57}$ $\Delta^{58}$ | J-482-11 |
| 11. | TYR$^{26}$ → ALA$^{26}$ | S-3123-2 |
| 12. | TYR$^{26}$ → CYS$^{26}$ | S-3140-22 |
| 13. | CYS$^{41}$ → ALA$^{41}$ | S-2515-5-10 |
| 14. | CYS$^{41}$ → SER$^{41}$ | S-3124-6 |
| 15. | CYS$^{201}$ → ALA$^{201}$ | S-2679-3-4 |
| 16. | GLU$^{129}$ → $\Delta^{129}$ | S-2589-6 |
| 17. | GLU$^{129}$ → GLY$^{129}$ | S-2515-3-6 |
| 18. | GLU$^{129}$ → GLN$^{129}$ | S-2515-1-2 |
| 19. | GLU$^{129}$ → ASP$^{129}$ | S-2515-2-4 |
| 20. | GLU$^{129}$ → ASN$^{129}$ | S-2852-1-18 |

TABLE 1a-continued

Summary of Mutations introduced into Pertussis Toxin

| Mutation Number | Mutation | Clone No. |
|---|---|---|
| 21. | GLU$^{129}$ –> LYS$^{129}$ | S-2515-4-11 |
| 22. | GLU$^{129}$ –> ARG$^{129}$ | M-32-2-4 |
| 23. | GLU$^{129}$ –> HIS$^{129}$ | S-2937-1-2 |
| 24. | GLU$^{129}$ –> PRO$^{129}$ | S-2959-2-28 |
| 25. | GLU$^{129}$ –> CYS$^{129}$ | J-478-5 |
| 26. | GLU$^{129}$ –> GLY$^{129}$ II | J-418-1 |
| 27. | GLU$^{129}$ –> GLN$^{129}$ II | J-412-9 |
| 28. | TYR$^{130}$ –> $\Delta^{130}$ | S-2852-2-1 |
| 29. | TYR$^{130}$ –> PHE$^{130}$ | S-2836-15 |
| 30. | GLU$^{129}$ TYR$^{130}$ –> GLY$^{129}$ ALA$^{130}$ | S-2679-4-3 |
| 31. | GLU$^{129}$ TYR$^{130}$ –> GLN$^{129}$ ALA$^{130}$ | M-38-1 |
| 32. | GLU$^{129}$ TYR$^{130}$ –> GLY$^{129}$ PHE$^{130}$ | J-444-1-6 |
| 33. | (S3)LYS$^{10}$ –> GLN$^{10}$ | S-2995-1-2 |
| 34. | (S3)TYR$^{92}$ LYS$^{93}$ –> ASN$^{92}$ ARG$^{93}$ | S-2995-2-1 |
| 35. | (S3)LYS$^{105}$ –> ASN$^{105}$ | S-2995-3-1 |
| 36. | CYS$^{41}$ CYS$^{20}$ –> ALA$^{41}$ ALA$^{201}$ | S-2818-1 |
| 37. | CYS$^{41}$ GLU$^{129}$ –> ALA$^{41}$ GLY$^{129}$ | S-2549-2 |
| 38. | ARG$^{9}$ GLU$^{129}$ –> GLU$^{9}$ GLY$^{129}$ II | S-2966-1-5 |
| 39. | ARG$^{9}$ GLU$^{129}$ –> GLU$^{9}$ GLN$^{129}$ II | S-2967-1-1 |
| 40. | ARG$^{9}$ GLU$^{129}$ –> GLU$^{9}$ ARG$^{129}$ | M-45-1 |
| 41. | ARG$^{9}$ GLU$^{129}$ TYR$^{130}$ –> GLU$^{9}$ GLY$^{129}$ ALA$^{130}$ | S-2956-1 |
| 42. | ARG$^{13}$ GLU$^{129}$ –> GLU$^{13}$ GLY$^{129}$ II | S-2966-2-13 |
| 43. | ARG$^{13}$ GLU$^{129}$ –> GLU$^{13}$ GLN$^{129}$ II | S-2967-2-17 |
| 44. | ARG$^{13}$ GLU$^{129}$ TYR$^{130}$ –> GLU$^{13}$ GLY$^{129}$ ALA$^{130}$ | S-2961-1 |
| 45. | ARG$^{9}$ GLU$^{129}$ –> $\Delta^{9}$ GLN$^{129}$ | S-2730-1-1 |
| 46. | ARG$^{9}$ GLU$^{129}$ TYR$^{130}$ –> $\Delta^{9}$ GLY$^{129}$ ALA$^{130}$ | S-2730-3-2 |
| 47. | ARG$^{13}$ GLU$^{129}$ –> $\Delta^{13}$ GLN$^{129}$ | S-2730-2-1 |
| 48. | ARG$^{13}$ GLU$^{129}$ TYR$^{130}$ –> $\Delta^{13}$ GLY$^{129}$ ALA$^{130}$ | S-2730-4-1 |
| 49. | GLU$^{129}$ –> GLY$^{129}$ <br> (S3)TYR$^{92}$ LYS$^{93}$    (S3)ASN$^{92}$ ARG$^{93}$ | S-3050-1 |
| 50. | Wild Type | S-2505-4-5 |

Amino acid numbering corresponds to positions in the native subunits (FIG. 5)
All mutations are in subunit S1 unless specified as being in S3 (S3)
II denotes use of an alternative codon
Δ denotes deleted residue(s)
Wild type refers to PT expressed from the unmutated TOX operon in *B. parapertussis*.

TABLE 1b

In vitro characterization of pertussis toxin analogues obtained from recombinant *B. parapertussis*.

| Mutation Number | Residual Toxicity | ADPR Activity | S1 Epitope |
|---|---|---|---|
| 1. | 0.2 | ND | − |
| 2. | 0.1 | 0.2 | +/− |
| 3. | 0.1 | ND | ++++ |
| 4. | 0.2 | 0.1 | +++ |
| 5. | 0.3 | ND | − |
| 6. | 5.0 | ND | ++++ |
| 7. | 0.4 | 0.1 | − |
| 8. | 0.1 | 0.9 | − |
| 9. | 0.7 | 0.6 | +++ |
| 10. | 0.4 | ND | − |
| 11. | 0.5 | ND | + |
| 12. | 6.0 | ND | ND |
| 13. | 0.3 | 0.4 | − |
| 14. | 1.4 | ND | ND |
| 15. | 0.2 | 0.1 | − |
| 16. | 0.1 | ND | ++ |
| 17. | 0.1 | 0.3 | ++++ |
| 18. | 0.02 | 0.1 | +/− |
| 19. | 0.7 | 2.5 | ++ |
| 20. | 0.1 | 0.3 | ++ |
| 21. | 0.3 | 0.2 | − |
| 22. | 0.1 | ND | − |
| 23. | 0.2 | ND | − |
| 24. | 0.2 | ND | + |
| 25. | 0.4 | ND | − |
| 26. | 0.1 | 0.3 | ++++ |
| 27. | 0.02 | 0.1 | +/− |
| 28. | 0.2 | 0.1 | − |
| 29. | 12.0 | ND | ++++ |
| 30. | 0.2 | 0.6 | − |
| 31. | 0.4 | ND | − |
| 32. | 1.0 | ND | ++++ |
| 33. | 100 | ND | +++++ |
| 34. | 50 | 100 | ++++ |
| 35. | 20 | ND | ++++ |
| 36. | 0.2 | 0.1 | − |
| 37. | 0.1 | 0.1 | − |
| 38. | 0.1 | 0.1 | − |
| 39. | 0.1 | ND | − |
| 40. | 0.1 | ND | − |
| 41. | 0.2 | ND | − |
| 42. | 0.5 | ND | − |
| 43. | 3.0 | ND | − |
| 44. | 0.3 | ND | − |
| 45. | 0.4 | ND | − |
| 46. | 0.2 | 0.1 | − |
| 47. | 0.5 | ND | − |
| 48. | 0.4 | 0.3 | − |
| 49. | 0.2 | 0.1 | +++ |
| 50. | 100 | 100 | ++++ |

Residual toxicity is the ratio of the apparent PT concentration determined by the CHO cell clustering assay to the actual concentration of PT mutant determined by ELISA expressed as a percentage.
ADPR activity is the extent of ADP-ribosylation of bovine transducin catalysed by a PT analogue, relative to that catalysed by an equal concentration of wild-type PT, expressed as a percentage.
S1 epitope refers to the expression of an immunodominant S1 epitope recognized by a specific monoclonal antibody PS21, as compared with the wild-type PT (+++++).
ND denotes not determined.

TABLE 2

Biological Activity of PT mutants in mice

| Analogue | Acute Toxicity LD$_{50}$ (ug) | HS Activity LD$_{50}$ (ug) | M.P.T. ED$_{50}$ (ug) |
|---|---|---|---|
| Native | ~2 | ~0.2 | ~2 |
| GLY$^{129}$ | >5 | ~3 | ~2 |

TABLE 2-continued

Biological Activity of PT mutants in mice

| Analogue | Acute Toxicity LD$_{50}$ (ug) | HS Activity LD$_{50}$ (ug) | M.P.T. ED$_{50}$ (ug) |
|---|---|---|---|
| GLN$^{129}$ | >16 | >3 | 16 |
| ASN$^{129}$ | >5 | ~3 | 1.5 |
| GLU$^{58}$ | >5 | 1.5 | 8.5 |
| LYS$^9$ | 0 | 6 | 2 |
| GLY$^{129}$ (S3)ASN$^{92}$ ARG$^{93}$ | >20 | 7 | 2 |
| (S3)ASN$^{92}$ ARG$^{93}$ | 3 | 0.4 | >2 |

HS Activity denotes histamine sensitizing activity.
M.P.T. denotes mouse intracerebral challenge protection test.
LD$^{50}$ is the dose resulting in death of 50% of the test animals.
ED$^{50}$ is the dose resulting in protection of 50% of the test animals.
Native denotes PT from *B. pertussis* 10536.

TABLE 3

Neutralizing effect of immune sera on PT-induced CHO cell clustering

| Analogue Dose (ug) | Pre-bleed | Post-1 bleed | Post-2 bleed |
|---|---|---|---|
| GLY$^{129}$ | | | |
| 2.0 | <2 | <2 | 256 |
| 0.5 | <2 | <2 | 128 |
| 0.125 | <2 | <2 | 64 |
| GLN$^{129}$ | | | |
| 2.0 | <2 | <2 | 128 |
| 0.5 | <2 | <2 | 256 |
| 0.125 | <2 | <2 | 128 |
| ASN$^{129}$ | | | |
| 2.0 | <2 | <2 | 512 |
| 0.5 | <2 | <2 | 128 |
| 0.125 | <2 | <2 | 256 |
| Saline | <2 | <2 | <2 |

Mice were pre-bled and immunized on day 0. On day 23 they were bled again (post-1 bleed) and boosted. Final sera were obtained on day 37 (post-2 bleed).
The neutralizing ability of the sera is expressed as the maximum dilution at which CHO cell clustering was inhibited.

TABLE 4

Specific antibody titres of immune sera

| Analoge Dose (ug) | Pre-bleed | | | Post-1 bleed | | | Post-2 bleed | | |
|---|---|---|---|---|---|---|---|---|---|
| GLY$^{129}$ | | | | | | | | | |
| 2.0 | NR | NR | NR | 63 | 2 | 50 | 500 | 80 | 200 |
| 0.5 | NR | NR | NR | 13 | 1 | 8 | 160 | 32 | 56 |
| 0.125 | NR | NR | NR | 10 | 0.5 | 8 | 200 | 32 | 80 |
| GLN$^{129}$ | | | | | | | | | |
| 2.0 | NR | NR | NR | 22 | 0.7 | 20 | 200 | 40 | 125 |
| 0.5 | NR | NR | NR | 8 | 0.5 | 6 | 200 | 40 | 100 |
| 0.125 | NR | NR | NR | 5 | <0.5 | 2 | 125 | 20 | 50 |
| ASN$^{129}$ | | | | | | | | | |
| 2.0 | NR | NR | NR | 40 | 1 | 40 | 500 | 140 | 280 |
| 0.5 | NR | NR | NR | 7 | <0.5 | 3 | 316 | 22 | 80 |
| 0.125 | NR | NR | NR | 7 | <0.5 | 4 | 180 | 63 | 125 |
| Saline | NR | NR | NR | NR | NR | NR | NR | NR | NR |

Immunization and bleeding were performed as described in Table 3.
Antigens used were PT holotoxin, isolated S1 subunit and isolated B oligomer.
The units are the dilution factor divided by 1000 giving an ELISA absorbance value equal to twice the background.
NR denotes not reactive with antigen.

TABLE 5

In vitro characterization of pertussis toxin analogues from recombinant *B. pertussis*

| Mutation Number | Clone | Residual Toxicity | ADPR Activity | S1 Epitope |
|---|---|---|---|---|
| 9 | S-3026-2 | 0.2 | 0.3 | +++ |
| 13 | S-3122-3-1 | 0.1 | ND | ND |
| 17 | S-2962-1-2 | 0.2 | ND | ND |
| 18 | S-2962-2-1 | 0.1 | ND | ND |
| 34 | S-3122-3-1 | 50 | ND | +++++ |
| 49 | S-3122-2-3 | 0.1 | ND | +++ |
| 50 | S-3006-3 | 100 | 100 | ++++ |

All terms are as defined in Tables 1a and 1b.
ND denotes not determined.

What we claim is:

1. An immunoprotective genetically detoxified mutant of pertussis holotoxin.
2. The mutant of claim 1 formed by genetic modification of the A portion (S1 subunit) of the holotoxin.
3. The mutant of claim 1 formed by genetic modification of the B portion of the holotoxin.
4. The mutant of claim 1 formed by genetic modification of both the A and B portions of the holotoxin.
5. The mutant of claim 1 wherein a single amino acid in the native pertussis holotoxin is removed or replaced.
6. The mutant of claim 5, wherein said single amino acid is GLU$^{129}$ and is removed.
7. The mutant of claim 5, wherein said single amino acid is GLU$^{129}$ and is replaced by GLY$^{129}$.
8. The mutant of claim 5 wherein said single amino acid is ARG$^{58}$ and is replaced by GLU$^{58}$.
9. The mutant of claim 1 wherein multiple amino acids in the native pertussis toxin are removed or replaced.
10. The mutant of claim 9 wherein said multiple amino acids are GLU$^{129}$ TYR$^{130}$ and are replaced by GLY$^{129}$ PHE$^{130}$.
11. The mutant of claim 9 wherein said multiple amino acids are GLU$^{129}$/(S3)TYR$^{92}$LYS$^{93}$ and are replaced by GLY$^{129}$/(S3)ASN$^{92}$ARG$^{93}$.
12. The mutant of claim 1 having a residual toxicity less than about 0.5% of the toxicity of the native toxin.
13. The mutant of claim 1 produced by site-directed mutagenesis of the native pertussis toxin gene.
14. The mutant of claim 1 having a decreased histamine sensitivity activity.
15. A vaccine against *Bordetella pertussis*, comprising an effective amount of an immunoprotective genetically-detoxified mutant of pertussis holotoxin or a toxoid thereof, and a physiologically-acceptable carrier therefor.
16. A conjugate vaccine, comprising an effective amount of an active conjugate comprising a genetically-detoxified mutant of pertussis holotoxin covalently bonded to a hapten, polysaccharide or polypeptide to elicit an antibody response to said hapten, polysaccharide or polypeptide.

* * * * *

UNITED STATES PATENT AND TRADEMARK OFFICE
CERTIFICATE OF CORRECTION

PATENT NO. : 5,085,862
DATED : February 4, 1992
INVENTOR(S) : Michel H. Klein et al It is certified that error appears in the above-indentified patent and that said Letters Patent is hereby corrected as shown below:

Col. 5, line 10, "November 24" should read --November 23--.

Col. 16, line 46, after "J-229-17" insert --(deposited with ATCC on November 30, 1989 under accession number 40715)--.

Col.17, line 25, after "str29" insert --(deposited with ATCC on November 30, 1989 under ATCC accession number 53,973)--.

Signed and Sealed this

Thirtieth Day of November, 1993

BRUCE LEHMAN

Attest:

Attesting Officer

Commissioner of Patents and Trademarks

Adverse Decision in Interference

Patent No. 5,085,862, Michel H. Klein, Heather A. Boux, Stephen A. Cockle, Sheena M. Loosmore, Gavin R. Zealey, GENETIC DETOXIFICATION OF PERTUSSIS TOXIN, Interference No. 105,101, final judgment adverse to the patentees rendered August 11, 2006, as to claims 1, 2, 5-7, 12-15.

*(Official Gazette February 13, 2007)*